US007067136B2

(12) United States Patent
Jackson et al.

(10) Patent No.: US 7,067,136 B2
(45) Date of Patent: Jun. 27, 2006

(54) METHOD OF SCREENING ANTI-MYCOBACTERIAL MOLECULES

(75) Inventors: Mary Jackson, Paris (FR); Brigitte Gicquel, Paris (FR)

(73) Assignee: Institut Pasteur, Paris (FR)

( * ) Notice: Subject to any disclaimer, the term of this patent is extended or adjusted under 35 U.S.C. 154(b) by 82 days.

(21) Appl. No.: 10/914,165

(22) Filed: Aug. 10, 2004

(65) Prior Publication Data

Related U.S. Application Data

(62) Division of application No. 10/383,675, filed on Mar. 10, 2003, now abandoned, which is a division of application No. 09/429,370, filed on Oct. 28, 1999, now Pat. No. 6,573,064.

(60) Provisional application No. 60/198,229, filed on Oct. 28, 1998, provisional application No. 60/113,675, filed on Nov. 4, 1998, provisional application No. 60/111,813, filed on Dec. 11, 1998.

(51) Int. Cl.
*A61K 39/02* (2006.01)
*A61K 39/04* (2006.01)
*A61K 39/40* (2006.01)

(52) U.S. Cl. ............ 424/200.1; 424/9.1; 424/9.2; 424/130.1; 424/164.1; 424/168.1; 424/185.1; 424/192.1; 424/199.1; 424/234.1; 424/248.1; 435/4; 435/29; 435/32; 435/183; 435/253.1

(58) Field of Classification Search .......... 424/9.1, 424/9.2, 130.1, 164.1, 168.1, 185.1, 192.1, 424/199.1, 200.1, 234.1, 248.1, 246.1; 435/4, 435/29, 32, 183, 253.1
See application file for complete search history.

(56) References Cited

U.S. PATENT DOCUMENTS

| 3,928,140 A | 12/1975 | Wyatt et al. |
| 4,320,200 A | 3/1982 | Higashide et al. |
| 6,010,855 A | 1/2000 | Jackson et al. |

OTHER PUBLICATIONS

NCBI Sequence Accession No. U49839, submitted Feb. 23, 1996, and Nov. 17, 1997.
Lim et al., "Identification of *Mycobaterium tuberulosis* DNA Sequences Encoding Exported Proteins by Using *phoA* Gene Fusions", *J. Bacteriology*, vol. 177, No. 1, pp. 59-65 (Jan. 1995).
Jackson et al., *Infection and Immunity*, vol. 65, pp. 3882-2889 (Jul. 1997).
Philipp et al., *Proc. Nat'l. Acad. Sci. U.S.A.*, vol. 93, pp. 3132-3137 (Apr. 1996).
Jackson et al., U.S. Appl. No. 09/422,662 (Oct. 22, 1999).
Altschul, S.F., et al. Basic local alignment search tool. Journal of Molecular Biology. 215:403-410 (1990).
Andersen, A.B., and B. Brennan. Proteins and antigens of *Mycobacterium tuberculosis*, p. 307-332. In B.R. Bloom (ed.), Tuberculosis: Pathogenesis, Protection, and Control. ASM, Washington, DC. (1994).
Andersen, P. Effective vaccination of mice against *Mycobacterium tuberculosis* infection with a soluble mixture of secreted mycobacterial proteins. Infect. Immun. 62:2536-2544 (1994).
Berthet, F.X., et al. Characterization of the *M. tuberculosis* erp gene encoding a potential cell surface protein with repetitive structures, Microbiology. 141:2123-2130 (1995).
de Boer, H.A., et al., The tac promoter: a functional hybrid derived from the trp and lac promoters. Proc. natl. Acad. Sci. USA 80, 21-25 (1983).
Braibant, M., et al. Structure of the *Mycobacterium tuberculosis* antigen 88, a protein related to the *Escherichia coli* PstA periplasmic phosphate permease subunit. Infection and Immunity. 62:849-854 (1994).
Cahoon, E.B., et al. Redesign of soluble fatty acid desaturases from plants for altered substrate specificity and double bond position. Proc. Nat'l. Acad. Sci. USA 94 (10), pp. 4872-4877 (1997).
Crowe, J. et al., K. 6XHIS-Ni-NTA chromatography as a superior technique in recombinant protein expression/purification. Methods Mol. Biol. 31, 371-387 (1994).
Fox, B.G. et al., Resonance Raman evidence for an Fe-O-Fe center in stearoyl-ACP desaturase. Primary sequence identity with other diiron-oxo proteins. Biochemistry. 33: 12776-12786 (1994).

(Continued)

*Primary Examiner*—Rodney P Swartz
(74) *Attorney, Agent, or Firm*—Finnegan, Henderson, Farabow, Garrett & Dunner, L.L.P.

(57) ABSTRACT

This invention relates to a novel mycobacterial protein named DES, which appears to share significant amino acid sequence homology with soluble stearoyl-ACP desaturases. The results of allelic exchange experiments, indicate that the des gene may be essential to the survival of mycobacteria. These results coupled with the surface localization, the unique structure of DES, and the fact this antigen is expressed in vivo, and DES protein induces a humoral response in human patients, indicate that the DES protein provides a new target for the design of anti-mycobacterial drugs. This invention provides methods of screening molecules that can inhibit the DES enzyme activity of purified DES protein, in order to identify antibiotic molecules that are capable of inhibiting the growth or survival of mycobacteria. These methods may be practiced by using recombinant DES protein obtained from a recombinant *mycobacterium* host cell that was transformed with a vector containing the des gene, whose expression is controlled by regulatory or promoter sequences that function in mycobacteria. Another aspect of this invention relates to the molecules that have been identified according to the screening methods as having antibiotic activity, against mycobacteria.

4 Claims, 14 Drawing Sheets

OTHER PUBLICATIONS

Fulco, A.J. and K. Bloch. Cofactor requirements for fatty acid desaturation in *Mycobacterium phlei*. Biochim. Biophys. Acta 63:545-546 (1962).

Fulco, A.J., and K. Bloch. Cofactor requirements for the formation of $\Delta^9$ unsaturated fatty acids in *Mycobacterium phlei*. The Journal of Biological Chemistry. 239:993-997 (1964).

Garbe, T., et al. Expression of the *Mycobacterium tuberculosis* 19-kilodalton antigen in *Mycobacterium smegmatis*: immunological analysis and evidence of glycosylation. Infect. Immun. 61, 260-267 (1993).

Gordon, S., et al., The application of luciferase as a reporter of environmental regulation of gene expression in *Mycobacteria*. Lett. Appl. Microbiol. 19, 336-340 (1994).

Hasløv, K., et al., Guinea pig cellular immune responses to proteins secreted by *Mycobacterium tuberculosis*. Infection and Immunity, 63:804-810 (1995).

Hatfull, G.F, Genetic transformation of *Mycobacteria*. Trends in microbiology. 1:310-314 (1993).

Hermans, P.W.M., et al. Molecular and immunological characterization of the highly conserved antigen 84 from *Mycobacterium tuberculosis* and *Mycobacterium leprae*. Infection and Immunity, 63:954-960 (1995).

Horsburgh, C.R. *Mycobacterium avium* complex infections in the acquired immunodeficiency syndrome. New England, Journal of Medicine, vol. 34, pp. 1332-1338 (1991).

Izard, J.W., and D.A. Kendall. Signal peptides: exquisitely designed transport promoters. Molecular Microbiology. 13:765-773 (1994).

Jacobs, W.R., et al., Genetic systems for *Mycobacteria*. Methods Enzymol. 204:537-555 (1991).

Kashiwabara, Y., and R. Sato. Electron transfer mechanism involved in stearoyl-coenzyme A desaturation by particulate fraction of *Mycobacterium phlei*. J. Biochem. 74:405-413 (1973).

Keegstra, K., and L.J. Olsen. Chloroplastic precursors and their transport across the envelope membranes. Ann. Rev. Plant Physiol. Plant Mol. Biol. 40:471-501 (1989).

Laemmli, U.K. Cleavage of structural proteins during the assembly of the head of bacteriophage T4. Nature (London). 227:680-685 (1970).

Lee, B.Y., et al., Characterization of the major membrane protein of virulent *Mycobacterium tuberculosis*. Infection and Immunity. 60:2066-2074 (1992).

Legrand, P., and A. Bensadoun. Stearoyl-CoA desaturase activity in cultured rat hepatocytes. Biochimica et Biophysica Acta. 1086:89-94 (1991).

Lindqvist, Y., et al., Crystal structure of $\Delta^9$ stearoyl-acyl carrier protein desaturase from castor seed and its relationship to other di-iron proteins. EMBO J. 15(16):4081-92 (1996).

Mahenthiralingam, E., et al., Cloning and sequencing of the gene which encodes the highly inducible acetamidase of *Mycobacterium smegmatis*. J. Gen. Microbiol. 139, 575-583 (1993).

Pal, P.G., and M.A. Horwitz: Immunization with extracellular proteins of *Mycobacterium tuberculosis* induces cell-mediated immune responses and substantial protective immunity in a guinea pig model of pulmonary tuberculosis. Infection and Immunity. 60:4781-4792 (1992).

Parish, T., et al., Regulation of inducivle acetamidase gene of *Mycobacterium smegmatis*. Microbiology 143, 2267-2276 (1997).

Parish, T. and Stocker, N.G. Development and use of a conditional antisense mutagenesis system in *Mycobacteria*. FEMS Microbiol. Lett. 154, 151-157 (1997).

Pellcic et al.: Efficient allelic exchange and transposon mutagenesis in *Mycobacterium tuberculosis*. Proc. Natl. Sci. USA, 94:10955-10960 (1997).

Pellcic et al.: Generation of unmarked directed mutations in *Mycobacteria*, using sucrose counter-selectable suicide vectors. Mol. Microbiol., 20:919-925 (1996).

M. Picardeau and V. Vincent:: Development of a species-specific probe for *Mycobacterium xenopi* Res. Microbiol., 46:237-263 (1995).

Roche, P.W., et al., Expression of *Mycobacterium tuberculosis* MPT64 in recombinant *M. smegmatis*: purification, immunogenicity and application to skin tests for tuberculosis. Clin. Exp. Immunol. 103, 226-232 (1996).

Romain, F., et al., Identification of a *Mycobacterium bovis* BCG 45/47—kilodalton antigen complex, an immunodominant target for antibody response after immunization with living bacteria. Infection and immunity. 61:742-750 (1993).

Sakamoto, t., et al. $\Delta 9$ acyl lipid desaturases of cyanobacteria. J. Biol. Chem. 269:25576-25580 91994).

Sanger, F. et al., DNA sequencing with chain terminating inhibitors. Proc. Natl. Acad. Sci. USA. 74:5463-5467 (1977).

Shanklin, J., and C. Somerville. Stearoyl-acyl-carrier-protein desaturase from higher plants is structurally unrelated to the animal and fungal homologs. Proceeding of the National Academy of Science of the United States of America. 88:2510-2514 (1991).

Shanklin, J., et al. Eight histidine residues are catalytically essential in a membrane-associated iron enzyme, stearoyl-CoA desaturase, and are conserved in alkane hydroxylase and xylene mono-oxygenase. Biochemistry. 33:12787-12794 (1994).

Snapper, S.B., et al., Molecular genetic approaches to mycobacterial investigation. p. 199-218. In J. McFadden (ed.), Molecular Biology of the mycobacteria. Surry University Press, London (1990).

Sorensen, A.L., et al. Purification and characterization of a low-molecular-mass T-cell antigen secreted by *Mycobacterium tuberculosis*. Infection and Immunity. 63:1710-1717 (1995).

Southern, E.M. Detection of specific sequences among DNA fragments separated by gel electrophoresis. J. Mol. Biol. 98:503-517 (1975).

Studier, W., A.H. Rosenberg, J.J. Dunn, and J.W. Dubendorff. Use of T7 RNA polymerase to direct expression of cloned genes. Methods in Enymology 185: 60-89 (1990).

Thole, J.E.R., and R.v.d. Zee. The 65 kDa antigen: molecular studies on a ubiquitous antigen., p. 37-66. In J. McFadden (ed.). Molecular Biology of the mycobacteria. Surrey University Press. London (1990).

Timm, J., et al., *Escherichia coli*-mycobacteria shuttle vectors for operon and gene fusions to *lacZ*: the pJEM series. J. Bacteriol. 176, 6749-6753 (1994).

Timm, J., et al., Transcription and expression analysis, using *lacZ* and *phoA* gene fusions, of *Mycobaterium fortuitum* b-lactamase genes cloned from a natural isolate and a high-level b-lactamase producer. Mol. Microbiol. 12, 491-504 (1994).

Triccass, J.A., et al., A 35 kDa protein is a major target of the human immune response to *Mycobacterium leprae*. Infect. Immun. 64: 5171-5177 (1996).

Wheeler, P.R., and C. Ratledge. Metabolism of *Mycobacterium tuberculosis*, p. 353-385. In B.R. Bloom (ed.), Tuberculosis: Pathogenesis, Protection, and Control. ASM, Washington DC (1994).

Winter, N., et al., Characterization of the gene encoding the immunodominant 35 kDa protein of *Mycobacterium leprae*. Mol. Microbiol. 16, 865-876 (1995).

Young, D., et al., Protein antigens: structure, function and regulation, p. 1-35. In J. McFadden (ed.). Molecular biology of *Mycobacteria*. Surry university Press, Laudon (1990).

Young, R.A., et al., Dissection of the *Mycobacterium tuberculosis* antigens using recombinant DNA. Proc. Natl. Acad. Sci. USA. 82:2583-2587 (1985).

Kashiwabara et al. Effect of Metal Ions in the Culture Medium on the Stearoyl-Coenzyme A Desaturase Activity of *Mycobacterium phlei*. J. Biochem. 78:803-810 (1975).

```
     S.D.                                                      BamHI      ScaI
taagagaaagggagtccac ATG CCC GAG GTA GTT TTC GGA TCC AGT ACT
                    Met Pro Glu Val Val Phe Gly Ser Ser Thr
```

```
 XbnI
TCT AGA CAC CAC CAC CAC CAC CAC TGA    SEQ ID NO: 44
Ser Arg His His His His His His  *     SEQ ID NO: 45
```

```
                                                         ─────Fe A site─────
         ─────B Helix─────                                        ─────C Helix─────

Ribonucleotide reductases v01555  049 EFYKFLFTFL AMA E KLVNEN IDELVTSFES HDIDHYYTEQKAM ENVH GETYA 099 (SEQ ID NO.6)
k02672  072 IFISNLKYQT LL D SIQGRSP NVALLPLISI PELETWVETWAFS ETIH SRSYT 123 (SEQ ID NO.7)

Hydrocarbon hydroxylases m58499  102 ETMKVVSNFL EVG E YNAIAA TGMLWDSAQA AEQKNGYLAQVL D EIRH THQCA 152 (SEQ ID NO.8)
x55394  102 ETMKVISNFL EVG E YNAIAA SAMLWDSATA AEQKNGYLAQVL D EIRH THQCA 152 (SEQ ID NO.9)
m60276  097 NALKLFLTAV SPL E YQAFQG FSRVGRQFSG AGARVACQMQAI D ELRH VQTQV 147 (SEQ ID NO.10)
m65106  092 STLKSHYGAI AVG E YAAVTG EGRMARFSKA PGNRNMATFGMM D ELRH GQLQL 142 (SEQ ID NO.11)

Stearoyl-ACP-desaturases m59857  133 LVGDMITEEA LPTYQTMLNT LDGVRDETGA SPTSWAIWTRAWTA E ENRH GDLLN 184 (SEQ ID NO.12)
m59858  133 LVGDMITEEA LPTYQTMLNT LDGVRDETGA SPTPWAIWTRAWTA E ENRH GDLLN 184 (SEQ ID NO.13)
m61109  133 LVGDMITEEA LPTYQTMLNT LDGVRDETGA SLTPWAVWTRAWTA E ENRH GDLLH 184 (SEQ ID NO.14)
x62898  136 LVGDMITEEA LPTYQTMLNT LDGAKDETGA SPTSWAVWTRAWTA E ENRH GDLLN 187 (SEQ ID NO.15)
x60978  135 LVGDMITEEA LPTYQTMLNT LDGVRDETGA SPTSWAIWTRAWTA E ENRH GDLLN 186 (SEQ ID NO.16)
m91238  130 LIGDMITEEA LPTYQTMLNT LDGVRDETGA TVTPWAIWTRAWTA E ENRH GDLLN 181 (SEQ ID NO.17)
x70962  133 LVGDMITEEA LPTYQTMINT LDGVRDETGA SLTPWAIWTRAWTA E ENRH GDLLN 184 (SEQ ID NO.18)
m93115  121 LVGDMITEEA LPTYMSMLNR CDGIKDDTGA QPTSWATWTRAWTA E ENRH GDLLN 172 (SEQ ID NO.19)

M. tuberculosis DES protein

Mtb.des  062 SDVAQVAMVQ NLVTEDNLPS YHREIAMNMG MDGAWGQWVNRWTA E ENRH GIALR 115 (SEQ ID NO.20)
```

FIG. 3A

—□— Average of tuberculous patients
(*M. tuberculosis*) (15 individuals)

—◇— Average of tuberculous patients
(*M. bovis*) (5 individuals)

—○— Average of non-tuberculous patients
(24 individuals)

FIG. 7A

```
   1 GATCATCATCGGCCGGCTGCCGCTGCCGCGAGGGCGCCGACACCGGCGAGTGCGGGGCGGAGGATCGGCCCCCAC
  71 CAGTTCGGCGCAGCTGCGTGCGTGATGCGCTCCACAATCCCGGGAAACAGCTCGACCATTACCTCCTCAATAT
 141 GAGCCTCGAAAAACTTGCCGCTGTGCCGGCTCGTGTGAGCGCACACAACAACTGTTAGCTGACCAGC
 211 AGGATCGGCGCTCTTACCGGTCTGTTCACCGATATCTGAACGGACGGTGGAGCCACCCGCAAGCAAT
 281 TCATCGACTACTGCGTCAACATGTTGCTCAGCACCGCCACCTACGCCCGCCACCGCGAGCGGGGAGA
 351 ATCCGAACACTCCATCCCCAGCCGGGCCGCACACTGAGGACGACTGGGGTTCACCCCACGGCCACCGG
                                                                    -35
 421 GGCCCGCCGATGCCAGCATCCTGCCCGCTGCTGGCAGCTCAACATGCCGAAGCCCAAAC TTGATGC
                      -10            +1
 491 TACCGAGAGACACAGA TATATTGACTGCAACCATTAGACACAGATAACT GGAGGCGCCATGTCAGCCAAG
                                                                  M S A K
 561 CTGACCGACCTGCAGCTGCTGCACGAACTTGAACCGGTCGTCGAGAAGTACCTGAACCGGCACCTGAGCA
      L T D L Q L L H E L E P V V E K Y L N R H L S M
 631 TGCACAAGCCCTGGAACCCTGACATCCCGTGGTCGACGGGAAGAACTACTACGCCCTCGGCGG
      H K P W N P H D Y I P W S D G K N Y Y A L G G
 701 GCAGGATTGGGACCCCGACCAGAGCAAGCTTTCTGATGTCGCCCAGGTGGCCGATGGTGCAGAACCTGGTC
      Q D W D P D Q S K L S D V A Q V A M V Q N L V
 771 ACCGAGGACAACCTGCCTTCGTATCACCGCGAGATCGCCATGAACATGGGCATGGACGGCGCGTGGGGGC
      T E D N L P S Y H R E I A M N M G M D G A W G Q
```

FIG. 7B

```
 841  AGTGGGTCAACCGTTGGACCGCCGAGGAGAATCGGCACGGCATCGCGCTGCGCGACTACCTGGTGGTGAC
       W  V  N  R  W  T  A  E  E  N  R  H  G  I  A  L  R  D  Y  L  V  V  T
 911  CCGATCGGTCGACCCTGTCGAGTTGGAGAAACTTCGCCTCCGAGGTAGTCAACGGGGTTCAGCCCAGC
       R  S  V  D  P  V  E  L  E  K  L  R  L  E  V  V  N  R  G  F  S  P  G
 981  CAAAACCAGGGCCACTATTTCGCGGAGAGCCTCACCGACTCCGTCCTCTATGTCAGTTTCCAGGAAC
       Q  N  H  Q  G  H  Y  F  A  E  S  L  T  D  S  V  L  Y  V  S  F  Q  E  L
1051  TGGCAACCCGGATTCGCACCGCAATACCGGCAAGGCATGTAACGACCCCGTCGCCGACCAGCTCATGGC
       A  T  R  I  S  H  R  N  T  G  K  A  C  N  D  P  V  A  D  Q  L  M  A
1121  CAAGATCTCGGCAGACGAGAATCTGCACATGATCTTCTACCGCGACGTCAGCGAGGCCGCGTTCGACCTC
       K  I  S  A  D  E  N  L  H  M  I  F  Y  R  D  V  S  E  A  A  F  D  L
1191  GTGCCCAACCAGGCCATGAAGTCGCTGCACCTTCCAGATGCCCGGCTTCCAAGTAC
       V  P  N  Q  A  M  K  S  L  H  L  I  L  S  H  F  Q  M  P  G  F  Q  V  P
1261  CCGAGTTCCGGGCGCAAAGCCTGGTCATCGCCGTGGTGTCATACGACCCGGCATCCACCTCGACGA
       E  F  R  R  K  A  V  V  I  A  V  G  G  V  Y  D  P  R  I  H  L  D  E
1331  AGTGGTCATGCCGGTACTGAAGAAAATGTGTATCTTCGAGCGGGAGGACTTCACCGGCGAGGGGCTAAG
       V  V  M  P  V  L  K  K  M  C  I  F  E  R  E  D  F  T  G  E  G  A  K
1401  CTGCGCGACGAGCTGGCCCTGGTGATCAAGGACCTCGAGCTGCTGCGACAAGTTCGAGGTGTCCAAGC
       L  R  D  E  L  A  L  V  I  K  D  L  E  L  A  C  D  K  F  E  V  S  K  Q
1471  AACGCCAACTCGACCGGGAAGCCCGTACGGGCAAGAAGGTCAGCGCACACGAGCTGCATAAAACCGCTGG
       R  Q  L  D  R  E  A  R  T  G  K  K  V  S  A  H  E  L  H  K  T  A  G
1541  CAAACTGGCGATGAGCCGTCGTTAGCCCGCGACGATGAGCGCAGCGCGATGAGC  (SEQ ID NO.36)
       K  L  A  M  S  R  R  *  (SEQ ID NO.37)
```

| Strain or plasmid | Relevant characteristics |
|---|---|
| E. coli DH5α | F/endA1 hsdR17(r$_k^-$m$_k^-$) supE44 thi-1 recA1 gyrA (Nal$^r$) relA1 Δ(lacZYA-argF)U169 deoR (Φ80fdlacΔ(lacZ)M15) |
| E. coli BL21(DE3)pLysS | F- ompT hsdS$_0$(r$_B^-$-m$_B^-$); an E. coli B strain) with a λ prophage carrying the T7 RNA polymerase gene. |
| M. smegmatis mc²155 | High transformation mutant of M. smegmatis ATCC607 |
| M. tuberculosis H37Rv | Virulent strain of mycobacterium originally isolated from tuberculosis patient |
| pBluescript KS- | Phagemid derived from pUC19 cloning vector |
| pYUB18 | (Km)$^R$ shuttle vector used for the construction of a M. tuberculosis cosmid library |
| pJEM11 | E.coli-mycobacterium shuttle vector carrying a truncated phoA gene |
| pET14b | pBR322 derivative containing a T7 promoter for expression of target DNAs. |
| pExp421 | pJEM11 vector carrying the 1.1 kb insert from the des-PhoA fusion |
| pBS-des | pBluescript KS- vector carrying the EcoRV 4.5kb insert containing the des gene |
| pET-des | pET14b vector carrying the (JD8-JD9)des PCR amplification product |

FIG. 8

1. Pool of sera from tuberculous cattle
2. Pool of sera from lepromatous leprosy patients
3. Individual sera from *M. bovis*-infected tuberculous patients
4. Individual sera from *M. tuberculosis*-infected tuberculous patients

SEQUENCE LISTING

<160> NUMBER OF SEQ ID NOS: 49

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 1
cggcatatgt cagccaagct gaccgacctg cag                33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 2
ccgggatccc gcgctcgccg ctctgcatcg tcg                33

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: DES motif
<220> FEATURE:
<221> NAME/KEY: MOD_RES
<222> LOCATION: (3)
<223> OTHER INFORMATION: Xaa = any amino acid
<220> FEATURE:
<221> NAME/KEY: MOD_RES
<222> LOCATION: (4)
<223> OTHER INFORMATION: Xaa = any amino acid

<400> SEQUENCE: 3

Glu Glu Xaa Xaa His
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: DES motif
<220> FEATURE:
<221> NAME/KEY: MOD_RES
<222> LOCATION: (3)
<223> OTHER INFORMATION: Xaa = any amino acid
<220> FEATURE:
<221> NAME/KEY: MOD_RES
<222> LOCATION: (4)
<223> OTHER INFORMATION: Xaa = any amino acid

<400> SEQUENCE: 4

Asp Glu Xaa Xaa His
 1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: DES motif
<220> FEATURE:
<221> NAME/KEY: MOD_RES

```
<222> LOCATION: (3)
<223> OTHER INFORMATION: Xaa = any amino acid
<220> FEATURE:
<221> NAME/KEY: MOD_RES
<222> LOCATION: (4)
<223> OTHER INFORMATION: Xaa = any amino acid
<220> FEATURE:
<221> NAME/KEY: MOD_RES
<222> LOCATION: (8)
<223> OTHER INFORMATION: Xaa = any amino acid
<220> FEATURE:
<221> NAME/KEY: MOD_RES
<222> LOCATION: (9)
<223> OTHER INFORMATION: Xaa = any amino acid

<400> SEQUENCE: 5

Asp Glu Xaa Xaa His Glu Glu Xaa Xaa His
  1               5                  10

<210> SEQ ID NO 6
<211> LENGTH: 52
<212> TYPE: PRT
<213> ORGANISM: Epstein Barr virus

<400> SEQUENCE: 6

Glu Phe Tyr Lys Phe Leu Phe Thr Phe Leu Ala Met Ala Glu Lys Leu
  1               5                  10                  15

Val Asn Phe Asn Ile Asp Glu Leu Val Thr Ser Phe Glu Ser His Asp
             20                  25                  30

Ile Asp His Tyr Tyr Thr Glu Gln Lys Ala Met Glu Asn Val His Gly
         35                  40                  45

Glu Thr Tyr Ala
    50

<210> SEQ ID NO 7
<211> LENGTH: 52
<212> TYPE: PRT
<213> ORGANISM: Escherichia coli

<400> SEQUENCE: 7

Ile Phe Ile Ser Asn Leu Lys Tyr Gln Thr Leu Leu Asp Ser Ile Gln
  1               5                  10                  15

Gly Arg Ser Pro Asn Val Ala Leu Leu Pro Leu Ile Ser Ile Pro Glu
             20                  25                  30

Leu Glu Thr Trp Val Glu Thr Trp Ala Phe Ser Glu Thr Ile His Ser
         35                  40                  45

Arg Ser Tyr Thr
    50

<210> SEQ ID NO 8
<211> LENGTH: 52
<212> TYPE: PRT
<213> ORGANISM: Methylococcus capsulatus

<400> SEQUENCE: 8

Glu Thr Met Lys Val Val Ser Asn Phe Leu Glu Val Gly Glu Tyr Asn
  1               5                  10                  15

Ala Ile Ala Ala Thr Gly Met Leu Trp Asp Ser Ala Gln Ala Ala Glu
             20                  25                  30

Gln Lys Asn Gly Tyr Leu Ala Gln Val Leu Asp Glu Ile Arg His Thr
         35                  40                  45

His Gln Cys Ala
    50
```

<210> SEQ ID NO 9
<211> LENGTH: 52
<212> TYPE: PRT
<213> ORGANISM: Methylosinus trichosporium

<400> SEQUENCE: 9

Glu Thr Met Lys Val Ile Ser Asn Phe Leu Glu Val Gly Glu Tyr Asn
1               5                   10                  15

Ala Ile Ala Ala Ser Ala Met Leu Trp Asp Ser Ala Thr Ala Ala Glu
            20                  25                  30

Gln Lys Asn Gly Tyr Leu Ala Gln Val Leu Asp Glu Ile Arg His Thr
        35                  40                  45

His Gln Cys Ala
        50

<210> SEQ ID NO 10
<211> LENGTH: 52
<212> TYPE: PRT
<213> ORGANISM: Pseudomonas sp.

<400> SEQUENCE: 10

Asn Ala Leu Lys Leu Phe Leu Thr Ala Val Ser Pro Leu Glu Tyr Gln
1               5                   10                  15

Ala Phe Gln Gly Phe Ser Arg Val Gly Arg Gln Phe Ser Gly Ala Gly
            20                  25                  30

Ala Arg Val Ala Cys Gln Met Gln Ala Ile Asp Glu Leu Arg His Val
        35                  40                  45

Gln Thr Gln Val
        50

<210> SEQ ID NO 11
<211> LENGTH: 52
<212> TYPE: PRT
<213> ORGANISM: Pseudomonas mendocina

<400> SEQUENCE: 11

Ser Thr Leu Lys Ser His Tyr Gly Ala Ile Ala Val Gly Glu Tyr Ala
1               5                   10                  15

Ala Val Thr Gly Glu Gly Arg Met Ala Arg Phe Ser Lys Ala Pro Gly
            20                  25                  30

Asn Arg Asn Met Ala Thr Phe Gly Met Met Asp Glu Leu Arg His Gly
        35                  40                  45

Gln Leu Gln Leu
        50

<210> SEQ ID NO 12
<211> LENGTH: 54
<212> TYPE: PRT
<213> ORGANISM: Ricinus communis

<400> SEQUENCE: 12

Leu Val Gly Asp Met Ile Thr Glu Glu Ala Leu Pro Thr Tyr Gln Thr
1               5                   10                  15

Met Leu Asn Thr Leu Asp Gly Val Arg Asp Glu Thr Gly Ala Ser Pro
            20                  25                  30

Thr Ser Trp Ala Ile Trp Thr Arg Ala Trp Thr Ala Glu Glu Asn Arg
        35                  40                  45

His Gly Asp Leu Leu Asn

<210> SEQ ID NO 13
<211> LENGTH: 54
<212> TYPE: PRT
<213> ORGANISM: Cucumis sativus

<400> SEQUENCE: 13

Leu Val Gly Asp Met Ile Thr Glu Glu Ala Leu Pro Thr Tyr Gln Thr
 1               5                  10                  15

Met Leu Asn Thr Leu Asp Gly Val Arg Asp Glu Thr Gly Ala Ser Pro
            20                  25                  30

Thr Pro Trp Ala Ile Trp Thr Arg Ala Trp Thr Ala Glu Glu Asn Arg
        35                  40                  45

His Gly Asp Leu Leu Asn
    50

<210> SEQ ID NO 14
<211> LENGTH: 54
<212> TYPE: PRT
<213> ORGANISM: Carthamus tinctorius

<400> SEQUENCE: 14

Leu Val Gly Asp Met Ile Thr Glu Glu Ala Leu Pro Thr Tyr Gln Thr
 1               5                  10                  15

Met Leu Asn Thr Leu Asp Gly Val Arg Asp Glu Thr Gly Ala Ser Leu
            20                  25                  30

Thr Pro Trp Ala Val Trp Thr Arg Ala Trp Thr Ala Glu Glu Asn Arg
        35                  40                  45

His Gly Asp Leu Leu His
    50

<210> SEQ ID NO 15
<211> LENGTH: 54
<212> TYPE: PRT
<213> ORGANISM: Spinacia oleracea

<400> SEQUENCE: 15

Leu Val Gly Asp Met Ile Thr Glu Glu Ala Leu Pro Thr Tyr Gln Thr
 1               5                  10                  15

Met Leu Asn Thr Leu Asp Gly Ala Lys Asp Glu Thr Gly Ala Ser Pro
            20                  25                  30

Thr Ser Trp Ala Val Trp Thr Arg Ala Trp Thr Ala Glu Glu Asn Arg
        35                  40                  45

His Gly Asp Leu Leu Asn
    50

<210> SEQ ID NO 16
<211> LENGTH: 54
<212> TYPE: PRT
<213> ORGANISM: Brassica rapa

<400> SEQUENCE: 16

Leu Val Gly Asp Met Ile Thr Glu Glu Ala Leu Pro Thr Tyr Gln Thr
 1               5                  10                  15

Met Leu Asn Thr Leu Asp Gly Val Arg Asp Glu Thr Gly Ala Ser Pro
            20                  25                  30

Thr Ser Trp Ala Ile Trp Thr Arg Ala Trp Thr Ala Glu Glu Asn Arg
        35                  40                  45

-continued

```
His Gly Asp Leu Leu Asn
     50

<210> SEQ ID NO 17
<211> LENGTH: 54
<212> TYPE: PRT
<213> ORGANISM: Solanum tuberosum

<400> SEQUENCE: 17

Leu Ile Gly Asp Met Ile Thr Glu Glu Ala Leu Pro Thr Tyr Gln Thr
  1               5                  10                  15

Met Ile Asn Thr Leu Asp Gly Val Arg Asp Glu Thr Gly Ala Thr Val
             20                  25                  30

Thr Pro Trp Ala Ile Trp Thr Arg Ala Trp Thr Ala Glu Glu Asn Arg
         35                  40                  45

His Gly Asp Leu Leu Asn
     50

<210> SEQ ID NO 18
<211> LENGTH: 54
<212> TYPE: PRT
<213> ORGANISM: Linum usitatissimum

<400> SEQUENCE: 18

Leu Val Gly Asp Met Ile Thr Glu Glu Ala Leu Pro Thr Tyr Gln Thr
  1               5                  10                  15

Met Leu Asn Thr Leu Asp Gly Val Arg Asp Glu Thr Gly Ala Ser Leu
             20                  25                  30

Thr Pro Trp Ala Ile Trp Thr Arg Ala Trp Thr Ala Glu Glu Asn Arg
         35                  40                  45

His Gly Asp Leu Leu Asn
     50

<210> SEQ ID NO 19
<211> LENGTH: 54
<212> TYPE: PRT
<213> ORGANISM: Coriandrum sativum

<400> SEQUENCE: 19

Leu Val Gly Asp Met Ile Thr Glu Glu Ala Leu Pro Thr Tyr Met Ser
  1               5                  10                  15

Met Leu Asn Arg Cys Asp Gly Ile Lys Asp Asp Thr Gly Ala Gln Pro
             20                  25                  30

Thr Ser Trp Ala Thr Trp Thr Arg Ala Trp Thr Ala Glu Glu Asn Arg
         35                  40                  45

His Gly Asp Leu Leu Asn
     50

<210> SEQ ID NO 20
<211> LENGTH: 54
<212> TYPE: PRT
<213> ORGANISM: Mycobacterium tuberculosis

<400> SEQUENCE: 20

Ser Asp Val Ala Gln Val Ala Met Val Gln Asn Leu Val Thr Glu Asp
  1               5                  10                  15

Asn Leu Pro Ser Tyr His Arg Glu Ile Ala Met Asn Met Gly Met Asp
             20                  25                  30

Gly Ala Trp Gly Gln Trp Val Asn Arg Trp Thr Ala Glu Glu Asn Arg
         35                  40                  45
```

```
His Gly Ile Ala Leu Arg
        50

<210> SEQ ID NO 21
<211> LENGTH: 52
<212> TYPE: PRT
<213> ORGANISM: Epstein Barr virus

<400> SEQUENCE: 21

Glu Lys Ile Leu Val Phe Leu Leu Ile Glu Gly Ile Phe Phe Ile Ser
  1               5                  10                  15

Ser Phe Tyr Ser Ile Ala Leu Leu Arg Val Arg Gly Leu Met Pro Gly
             20                  25                  30

Ile Cys Leu Ala Asn Asn Tyr Ile Ser Arg Asp Glu Leu Leu His Thr
         35                  40                  45

Arg Ala Ala Ser
        50

<210> SEQ ID NO 22
<211> LENGTH: 52
<212> TYPE: PRT
<213> ORGANISM: Escherichia coli

<400> SEQUENCE: 22

Leu Cys Leu Met Ser Val Asn Ala Leu Glu Ala Ile Arg Phe Tyr Val
  1               5                  10                  15

Ser Phe Ala Cys Ser Phe Ala Phe Ala Glu Arg Glu Leu Met Glu Gly
             20                  25                  30

Asn Ala Lys Ile Ile Arg Leu Ile Ala Arg Asp Glu Ala Leu His Leu
         35                  40                  45

Thr Gly Thr Gln
        50

<210> SEQ ID NO 23
<211> LENGTH: 52
<212> TYPE: PRT
<213> ORGANISM: Methylcoccus capsulatus

<400> SEQUENCE: 23

Cys Ser Leu Asn Leu Gln Leu Val Gly Glu Ala Cys Phe Thr Asn Pro
  1               5                  10                  15

Leu Ile Val Ala Val Thr Glu Trp Ala Ala Ala Asn Gly Asp Glu Ile
             20                  25                  30

Thr Pro Thr Val Phe Leu Ser Ile Glu Thr Asp Glu Leu Arg His Met
         35                  40                  45

Ala Asn Gly Tyr
        50

<210> SEQ ID NO 24
<211> LENGTH: 52
<212> TYPE: PRT
<213> ORGANISM: Methylosinus trichosporium

<400> SEQUENCE: 24

Cys Ser Val Asn Leu Gln Leu Val Gly Asp Thr Cys Phe Thr Asn Pro
  1               5                  10                  15

Leu Ile Val Ala Val Thr Glu Trp Ala Ile Gly Asn Gly Asp Glu Ile
             20                  25                  30

Thr Pro Thr Val Phe Leu Ser Val Glu Thr Asp Glu Leu Arg His Met
```

```
            35                  40                  45

Ala Asn Gly Tyr
     50

<210> SEQ ID NO 25
<211> LENGTH: 52
<212> TYPE: PRT
<213> ORGANISM: Pseudomonas sp.

<400> SEQUENCE: 25

Phe Leu Thr Ala Val Ser Phe Ser Glu Tyr Val Leu Thr Asn Leu
 1               5                  10                  15

Leu Phe Val Pro Phe Met Ser Gly Ala Ala Tyr Asn Gly Asp Met Ala
                20                  25                  30

Thr Val Thr Phe Gly Phe Ser Ala Gln Ser Asp Glu Ala Arg His Met
            35                  40                  45

Thr Leu Gly Leu
     50

<210> SEQ ID NO 26
<211> LENGTH: 52
<212> TYPE: PRT
<213> ORGANISM: Pseudomonas mendocina

<400> SEQUENCE: 26

Val Ala Ile Met Leu Thr Phe Ser Phe Glu Thr Gly Phe Thr Asn Met
 1               5                  10                  15

Gln Phe Leu Gly Leu Ala Ala Asp Ala Ala Glu Ala Gly Asp Tyr Thr
                20                  25                  30

Phe Ala Asn Leu Ile Ser Ser Ile Gln Thr Asp Glu Ser Arg His Ala
            35                  40                  45

Gln Gln Gly Gly
     50

<210> SEQ ID NO 27
<211> LENGTH: 52
<212> TYPE: PRT
<213> ORGANISM: Ricinus communis

<400> SEQUENCE: 27

Tyr Leu Gly Phe Ile Tyr Thr Ser Phe Gln Glu Arg Ala Thr Phe Ile
 1               5                  10                  15

Ser His Gly Asn Thr Ala Arg Gln Ala Lys Glu His Gly Asp Ile Lys
                20                  25                  30

Leu Ala Gln Ile Cys Gly Thr Ile Ala Ala Asp Glu Lys Arg His Glu
            35                  40                  45

Thr Ala Tyr Thr
     50

<210> SEQ ID NO 28
<211> LENGTH: 52
<212> TYPE: PRT
<213> ORGANISM: Cucumis sativus

<400> SEQUENCE: 28

Tyr Leu Gly Phe Ile Tyr Thr Ser Phe Gln Glu Arg Ala Thr Phe Ile
 1               5                  10                  15

Ser His Gly Asn Thr Ala Arg Leu Ala Lys Glu His Gly Asp Ile Lys
                20                  25                  30
```

Leu Ala Gln Ile Cys Gly Thr Ile Thr Ala Asp Glu Lys Arg His Glu
        35                  40                  45

Thr Ala Tyr Thr
    50

<210> SEQ ID NO 29
<211> LENGTH: 52
<212> TYPE: PRT
<213> ORGANISM: Carthamus tinctorius

<400> SEQUENCE: 29

Tyr Leu Gly Phe Ile Tyr Thr Ser Phe Gln Glu Arg Ala Thr Phe Val
 1               5                  10                  15

Ser His Gly Asn Thr Ala Arg His Ala Lys Asp His Gly Asp Val Lys
                20                  25                  30

Leu Ala Gln Ile Cys Gly Thr Ile Ala Ser Asp Glu Lys Arg His Glu
        35                  40                  45

Thr Ala Tyr Thr
    50

<210> SEQ ID NO 30
<211> LENGTH: 52
<212> TYPE: PRT
<213> ORGANISM: Spinacia oleracea

<400> SEQUENCE: 30

Tyr Leu Gly Phe Val Tyr Thr Ser Phe Gln Glu Arg Ala Thr Phe Val
 1               5                  10                  15

Ser His Gly Asn Ser Ala Arg Leu Ala Lys Glu His Gly Asp Leu Lys
                20                  25                  30

Met Ala Gln Ile Cys Gly Ile Ile Ala Ser Asp Glu Lys Arg His Glu
        35                  40                  45

Thr Ala Tyr Thr
    50

<210> SEQ ID NO 31
<211> LENGTH: 52
<212> TYPE: PRT
<213> ORGANISM: Brassica rapa

<400> SEQUENCE: 31

Tyr Leu Gly Phe Ile Tyr Thr Ser Phe Gln Glu Arg Ala Thr Phe Ile
 1               5                  10                  15

Ser His Gly Asn Thr Ala Arg Gln Ala Lys Glu His Gly Asp Leu Lys
                20                  25                  30

Leu Ala Gln Ile Cys Gly Thr Ile Ala Ala Asp Glu Lys Arg His Glu
        35                  40                  45

Thr Ala Tyr Thr
    50

<210> SEQ ID NO 32
<211> LENGTH: 52
<212> TYPE: PRT
<213> ORGANISM: Solanum tuberosum

<400> SEQUENCE: 32

Tyr Leu Gly Phe Val Tyr Thr Ser Leu Arg Lys Gly Val Thr Phe Val
 1               5                  10                  15

Ser His Gly Asn Thr Ala Arg Leu Ala Lys Glu His Gly Asp Met Lys
                20                  25                  30

-continued

```
Leu Ala Gln Ile Cys Gly Ser Ile Ala Ala Asp Glu Lys Arg His Glu
        35                  40                  45

Thr Ala Tyr Thr
    50

<210> SEQ ID NO 33
<211> LENGTH: 52
<212> TYPE: PRT
<213> ORGANISM: Linum usitatissimum

<400> SEQUENCE: 33

Tyr Leu Gly Phe Ile Tyr Thr Ser Phe Gln Glu Arg Ala Thr Phe Ile
  1               5                  10                  15

Ser His Gly Asn Thr Ala Arg Leu Ala Lys Asp His Gly Asp Met Lys
            20                  25                  30

Leu Ala Gln Ile Cys Gly Ile Ile Ala Ala Asp Glu Lys Arg His Glu
        35                  40                  45

Thr Ala Tyr Thr
    50

<210> SEQ ID NO 34
<211> LENGTH: 52
<212> TYPE: PRT
<213> ORGANISM: Coriandrum sativum

<400> SEQUENCE: 34

Tyr Met Gly Phe Ile Tyr Thr Ser Phe Gln Glu Arg Ala Thr Phe Ile
  1               5                  10                  15

Ser His Ala Asn Thr Ala Lys Leu Ala Gln His Tyr Gly Asp Lys Asn
            20                  25                  30

Leu Ala Gln Val Cys Gly Asn Ile Ala Ser Asp Glu Lys Arg His Ala
        35                  40                  45

Thr Ala Tyr Thr
    50

<210> SEQ ID NO 35
<211> LENGTH: 49
<212> TYPE: PRT
<213> ORGANISM: Mycobacterium tuberculosis

<400> SEQUENCE: 35

Thr Asp Ser Val Leu Tyr Val Ser Phe Gln Glu Leu Ala Thr Arg Ile
  1               5                  10                  15

Ser His Arg Asn Thr Gly Lys Ala Cys Asn Asp Pro Val Ala Asp Gln
            20                  25                  30

Leu Met Ala Lys Ile Ser Ala Asp Glu Asn Leu His Met Ile Phe Tyr
        35                  40                  45

Arg

<210> SEQ ID NO 36
<211> LENGTH: 1600
<212> TYPE: DNA
<213> ORGANISM: Mycobacterium tuberculosis
<220> FEATURE:
<221> NAME/KEY: CDS
<222> LOCATION: (549)..(1562)

<400> SEQUENCE: 36
gatcatcatc ggccggctgc cgcgcagggc gccgacaccg gcgagtgcgg gcgcgaggat     60
```

```
cggcccccac cagttcggca gctgcgtgtc gatgcgctcc acaatcccgg gaaacagctc    120
gaccattacc tcctcaatat gagcctcgaa aaacttgccg ctgtgcgcgg cgtcgtggtg    180
agcgcacaca caactgtta gctgaccagc aggatcggcg ctcttaccgg tctgttcacc    240
gcatatctga acggacggct gggagccacc cgcaagcaat tcatcgacta ctgcgtcaac    300
atgttgctca gcaccgccgc cacctacgca ccgcaccgcg agcggggaga atccgaacac    360
tccatcccag ccgggccgca caactgagga cgactggggt tcaccccacg cggccaccgg    420
cgcccgccga tgccagcatc ctgcccgctg ctggcagctc aacatgccgc gcgaagccca    480
aacttgatgc taccgagaga cacagatata ttgactgcaa ccattagaca cagataactg    540 gaggcgcc atg tca gcc aag ctg acc gac ctg cag ctg ctg cac gaa ctt     590
         Met Ser Ala Lys Leu Thr Asp Leu Gln Leu Leu His Glu Leu
           1               5                  10 gaa ccg gtc gtc gag aag tac ctg aac cgg cac ctg agc atg cac aag      638
Glu Pro Val Val Glu Lys Tyr Leu Asn Arg His Leu Ser Met His Lys
 15              20                  25                  30 ccc tgg aac ccg cac gac tac atc ccg tgg tcg gac ggg aag aac tac      686
Pro Trp Asn Pro His Asp Tyr Ile Pro Trp Ser Asp Gly Lys Asn Tyr
                 35                  40                  45 tac gcg ctc ggc ggg cag gat tgg gac ccc gac cag agc aag ctt tct      734
Tyr Ala Leu Gly Gly Gln Asp Trp Asp Pro Asp Gln Ser Lys Leu Ser
             50                  55                  60 gat gtc gcc cag gtg gcg atg gtg cag aac ctg gtc acc gag gac aac      782
Asp Val Ala Gln Val Ala Met Val Gln Asn Leu Val Thr Glu Asp Asn
         65                  70                  75 ctg ccg tcg tat cac cgc gag atc gcg atg aac atg ggc atg gac ggc      830
Leu Pro Ser Tyr His Arg Glu Ile Ala Met Asn Met Gly Met Asp Gly
     80                  85                  90 gcg tgg ggg cag tgg gtc aac cgt tgg acc gcc gag gag aat cgg cac      878
Ala Trp Gly Gln Trp Val Asn Arg Trp Thr Ala Glu Glu Asn Arg His
 95                 100                 105                 110 ggc atc gcg ctg cgc gac tac ctg gtg gtg acc cga tcg gtc gac cct      926
Gly Ile Ala Leu Arg Asp Tyr Leu Val Val Thr Arg Ser Val Asp Pro
                115                 120                 125 gtc gag ttg gag aaa ctt cgc ctc gag gta gtc aac cgg ggc ttc agc      974
Val Glu Leu Glu Lys Leu Arg Leu Glu Val Val Asn Arg Gly Phe Ser
            130                 135                 140 cca ggc caa aac cac cag ggc cac tat ttc gcg gag agc ctc acc gac     1022
Pro Gly Gln Asn His Gln Gly His Tyr Phe Ala Glu Ser Leu Thr Asp
        145                 150                 155 tcc gtc ctc tat gtc agt ttc cag gaa ctg gca acc cgg att tcg cac     1070
Ser Val Leu Tyr Val Ser Phe Gln Glu Leu Ala Thr Arg Ile Ser His
    160                 165                 170 cgc aat acc ggc aag gca tgt aac gac ccc gtc gcc gac cag ctc atg     1118
Arg Asn Thr Gly Lys Ala Cys Asn Asp Pro Val Ala Asp Gln Leu Met
175                 180                 185                 190 gcc aag atc tcg gca gac gag aat ctg cac atg atc ttc tac cgc gac     1166
Ala Lys Ile Ser Ala Asp Glu Asn Leu His Met Ile Phe Tyr Arg Asp
                195                 200                 205 gtc agc gag gcc gcg ttc gac ctc gtg ccc aac cag gcc atg aag tcg     1214
Val Ser Glu Ala Ala Phe Asp Leu Val Pro Asn Gln Ala Met Lys Ser
            210                 215                 220 ctg cac ctg att ttg agc cac ttc cag atg ccc ggc ttc caa gta ccc     1262
Leu His Leu Ile Leu Ser His Phe Gln Met Pro Gly Phe Gln Val Pro
        225                 230                 235 gag ttc cgg cgc aaa gcc gtg gtc atc gcc gtc ggg ggt gtc tac gac     1310
Glu Phe Arg Arg Lys Ala Val Val Ile Ala Val Gly Gly Val Tyr Asp
    240                 245                 250
```

```
ccg cgc atc cac ctc gac gaa gtc gtc atg ccg gta ctg aag aaa tgg    1358
Pro Arg Ile His Leu Asp Glu Val Val Met Pro Val Leu Lys Lys Trp
255                 260                 265                 270 tgt atc ttc gag cgc gag gac ttc acc ggc gag ggg gct aag ctg cgc    1406
Cys Ile Phe Glu Arg Glu Asp Phe Thr Gly Glu Gly Ala Lys Leu Arg
            275                 280                 285 gac gag ctg gcc ctg gtg atc aag gac ctc gag ctg gcc tgc gac aag    1454
Asp Glu Leu Ala Leu Val Ile Lys Asp Leu Glu Leu Ala Cys Asp Lys
        290                 295                 300 ttc gag gtg tcc aag caa cgc caa ctc gac cgg gaa gcc cgt acg ggc    1502
Phe Glu Val Ser Lys Gln Arg Gln Leu Asp Arg Glu Ala Arg Thr Gly
    305                 310                 315 aag aag gtc agc gca cac gag ctg cat aaa acc gct ggc aaa ctg gcg    1550
Lys Lys Val Ser Ala His Glu Leu His Lys Thr Ala Gly Lys Leu Ala
320                 325                 330 atg agc cgt cgt tagcccggcg acgatgcaga gcgcgcagcg cgatgagc          1600
Met Ser Arg Arg
335
```

<210> SEQ ID NO 37
<211> LENGTH: 338
<212> TYPE: PRT
<213> ORGANISM: Mycobacterium tuberculosis

<400> SEQUENCE: 37

```
Met Ser Ala Lys Leu Thr Asp Leu Gln Leu Leu His Glu Leu Glu Pro
1               5                   10                  15

Val Val Glu Lys Tyr Leu Asn Arg His Leu Ser Met His Lys Pro Trp
            20                  25                  30

Asn Pro His Asp Tyr Ile Pro Trp Ser Asp Gly Lys Asn Tyr Tyr Ala
        35                  40                  45

Leu Gly Gly Gln Asp Trp Asp Pro Asp Gln Ser Lys Leu Ser Asp Val
    50                  55                  60

Ala Gln Val Ala Met Val Gln Asn Leu Val Thr Glu Asp Asn Leu Pro
65                  70                  75                  80

Ser Tyr His Arg Glu Ile Ala Met Asn Met Gly Met Asp Gly Ala Trp
                85                  90                  95

Gly Gln Trp Val Asn Arg Trp Thr Ala Glu Glu Asn Arg His Gly Ile
            100                 105                 110

Ala Leu Arg Asp Tyr Leu Val Val Thr Arg Ser Val Asp Pro Val Glu
        115                 120                 125

Leu Glu Lys Leu Arg Leu Glu Val Val Asn Arg Gly Phe Ser Pro Gly
    130                 135                 140

Gln Asn His Gln Gly His Tyr Phe Ala Glu Ser Leu Thr Asp Ser Val
145                 150                 155                 160

Leu Tyr Val Ser Phe Gln Glu Leu Ala Thr Arg Ile Ser His Arg Asn
                165                 170                 175

Thr Gly Lys Ala Cys Asn Asp Pro Val Ala Asp Gln Leu Met Ala Lys
            180                 185                 190

Ile Ser Ala Asp Glu Asn Leu His Met Ile Phe Tyr Arg Asp Val Ser
        195                 200                 205

Glu Ala Ala Phe Asp Leu Val Pro Asn Gln Ala Met Lys Ser Leu His
    210                 215                 220

Leu Ile Leu Ser His Phe Gln Met Pro Gly Phe Gln Val Pro Glu Phe
225                 230                 235                 240

Arg Arg Lys Ala Val Val Ile Ala Val Gly Gly Val Tyr Asp Pro Arg
```

-continued

```
                    245                 250                 255
Ile His Leu Asp Glu Val Val Met Pro Val Leu Lys Lys Trp Cys Ile
            260                 265                 270

Phe Glu Arg Glu Asp Phe Thr Gly Glu Gly Ala Lys Leu Arg Asp Glu
            275                 280                 285

Leu Ala Leu Val Ile Lys Asp Leu Glu Leu Ala Cys Asp Lys Phe Glu
            290                 295                 300

Val Ser Lys Gln Arg Gln Leu Asp Arg Glu Ala Arg Thr Gly Lys Lys
305                 310                 315                 320

Val Ser Ala His Glu Leu His Lys Thr Ala Gly Lys Leu Ala Met Ser
                325                 330                 335

Arg Arg
```

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 38
cacggtacca agctttctag caga                                    24

<210> SEQ ID NO 39
<211> LENGTH: 53
<212> TYPE: DNA
<213> ORGANISM: Artificial Sequence
<220> FEATURE:
<223> OTHER INFORMATION: Description of Artificial Sequence: primer

<400> SEQUENCE: 39
gtcagtggtg gtggtggtgg tgtctagaag tactggatcc gaaaactacc tcg    53

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 40
tagctgcagg gatccatgac gtcggct                                 27

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 41
gtgtctagac ttgtactcat g                                       21

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 42
gggtctagaa cgacggctca tcgccagttt gcc                          33

```
<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 43
cccggatcca tgtcagccaa gctgaccgac ctg                               33

<210> SEQ ID NO 44
<211> LENGTH: 76
<212> TYPE: DNA
<213> ORGANISM: Artificial Sequence
<220> FEATURE:
<223> OTHER INFORMATION: Description of Artificial Sequence: DNA
      construct
<220> FEATURE:
<221> NAME/KEY: CDS
<222> LOCATION: (20)..(73)

<400> SEQUENCE: 44
taagagaaag ggagtccac atg ccc gag gta gtt ttc gga tcc agt act tct      52
                    Met Pro Glu Val Val Phe Gly Ser Ser Thr Ser
                     1               5                  10 aga cac cac cac cac cac cac tga                                    76
Arg His His His His His His
            15

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: amino acid
      sequence encoded by DNA construct

<400> SEQUENCE: 45

Met Pro Glu Val Val Phe Gly Ser Ser Thr Ser Arg His His His
 1               5                  10                  15

His His

<210> SEQ ID NO 46
<211> LENGTH: 15
<212> TYPE: DNA
<213> ORGANISM: Mycobacterium tuberculosis
<220> FEATURE:
<221> NAME/KEY: modified_base
<222> LOCATION: (7)..(12)
<223> OTHER INFORMATION: a, t, c or g

<400> SEQUENCE: 46
gaygarnnnn nncay                                                  15

<210> SEQ ID NO 47
<211> LENGTH: 15
<212> TYPE: DNA
<213> ORGANISM: Mycobacterium tuberculosis
<220> FEATURE:
<221> NAME/KEY: modified_base
<222> LOCATION: (7)..(12)
<223> OTHER INFORMATION: a, t, c or g

<400> SEQUENCE: 47
gargarnnnn nncay                                                  15
```

```
-continued

<210> SEQ ID NO 48
<211> LENGTH: 5
<212> TYPE: PRT
<213> ORGANISM: Mycobacterium tuberculosis

<400> SEQUENCE: 48

Asp Glu Asn Leu His
 1               5

<210> SEQ ID NO 49
<211> LENGTH: 5
<212> TYPE: PRT
<213> ORGANISM: Mycobacterium tuberculosis

<400> SEQUENCE: 49

Glu Glu Asn Arg His
 1               5
```

METHOD OF SCREENING ANTI-MYCOBACTERIAL MOLECULES

CROSS-REFERENCE TO RELATED APPLICATIONS

This application is a division of application Ser. No. 10/383,675, filed Mar. 10, 2003 now abandoned, which is a division of application Ser. No. 09/429,370, filed Oct. 28, 1999 (now U.S. Pat. No. 6,573,064 B1), which claims the benefit under 35 U.S.C. § 119 of U.S. Provisional Application No. 60/198,229, filed on Oct. 28, 1998, U.S. Provisional Application No. 60/113,675, filed on Nov. 4, 1998, and U.S. Provisional Application No. 60/111,813, filed Dec. 11, 1998.

BACKGROUND OF THE INVENTION

Tuberculosis and leprosy, caused by the bacilli from the *Mycobacterium tuberculosis* complex and *M. leprae*, respectively, are the two major mycobacterial diseases. Other mycobacteriosis caused by a typical mycobacteria such as *M. avium, M. xenopi*, and *M. kansasii* also represent major health problems worldwide.

*M. avium* is a predominant strain isolated from T.B. patients with AIDS (Horburgh et al., 1991) and *M. xenopi* along with *M. kansasii* and *M. avium*, is the main agent of pulmonary infections due to opportunist mycobacteria in HIV seronegative patients. (M. Picardeau et al., 1995).

In addition, these atypical mycobacteriosis are often difficult to cure because of the lack of efficient drugs specifically directed against atypical mycobacteria. Pathogenic mycobacteria have the ability to survive within host phagocytic cells. The pathology of the tuberculosis infection derives from the interactions between the host and the bacteria, resulting from the damage the host immune response causes on tissues (Andersen & Brennan, 1994). In addition, the protection of the host against mycobacteria infection also depends on interactions between the host and mycobacteria.

Identification of the bacterial antigens involved in these interactions with the immune system is essential for the understanding of the pathogenic mechanisms of mycobacteria and the host immunological response in relation to the evolution of the disease. It is also of great importance for the improvement of the strategies for mycobacterial disease control through vaccination and immunodiagnosis.

Through the years, various strategies have been followed for identifying mycobacterial antigens. Biochemical tools for fractionating and analyzing bacterial proteins permitted the isolation of antigenic proteins selected on their capacity to elicit B- or T-cell responses (Romain et al., 1993; Sorensen et al., 1995). The recent development of molecular genetic methods for mycobacteria (Jacobs et al., 1991; Snapper et al., 1990; Hatful, 1993; Young et al., 1985) allowed the construction of DNA expression libraries of both *M. tuberculosis* and *M. leprae* in the λgt11 vector and their expression in *E. coli*. The screening of these recombinant libraries using murine polyclonal or monoclonal antibodies and patient sera led to the identification of numerous antigens (Braibant et al., 1994; Hermans et al., 1995; Thole & van der Zee, 1990). However, most of them turned out to belong to the group of highly conserved heat shock proteins (Thole & van der Zee, 1990; Young et al., 1990).

The observation in animal models that specific protection against tuberculosis was conferred only by administration of live BCG vaccine, suggested that mycobacterial secreted proteins might play a major role in inducing protective immunity. These proteins were shown to induce cell-mediated immune responses and protective immunity in a guinea pig or a mouse model of tuberculosis (Pal & Horwitz, 1992; Andersen, 1994; Haslov et al., 1995). Recently, a genetic methodology for the identification of exported proteins based on PhoA gene fusions was adapted to mycobacteria by (Lim et al., 1995). It permitted the isolation of *M. tuberculosis* DNA fragments encoding exported proteins, including the already known 19 kDa lipoprotein (Lee et al., 1992) and the ERP protein similar to the *M. leprae* 28 kDa antigen (Berthet et al., 1995).

SUMMARY OF THE INVENTION

We have characterized a new *M. tuberculosis* exported protein named DES, identified by using the PhoA gene fusion methodology. The des gene, which seems conserved among mycobacterial species, encodes an antigenic protein highly recognized by human sera from both tuberculosis and leprosy patients but not by sera from tuberculous cattle. The results of allelic exchange experiments described in this application, indicate that the des gene is essential to the survival of mycobacteria.

The amino acid sequence of the DES protein contains two sets of motifs that are characteristic of the active sites of enzymes from the class II diiron-oxo protein family. Among this family, the DES protein presents significant homologies to soluble stearoyl-acyl carrier protein (ACP) desaturases. Three dimensional modeling demonstrates that the DES protein and the plant stearoyl-ACP desaturase share a conserved active site.

This invention also provides methods of identifying molecules capable of inhibiting the growth and/or survival of Mycobacteria species. In particular, the methods of this invention include screening molecules that can inhibit the activity of the DES protein. These methods comprise the steps of:

a) contacting the molecule with a strain of mycobacteria species containing an active DES protein or a DES like protein or a vector carrying an active DES protein gene or a vector containing a polynucleotide sequence encoding the active site of the DES protein;

b) measuring the inhibition of the growth of said mycobacteria strain; and c) identifying the molecule that is reacting with the DES protein or with the active site of said protein carrying conserved residues.

To practice the methods of this invention, the purified DES protein may be a recombinant desaturase protein. The recombinant DES protein can be obtained from a recombinant mycobacterium host cell that was transformed with an expression vector containing a polynucleotide encoding the DES protein whose expression is controlled by regulatory sequences that function in mycobacteria. In one method of the invention, the recombinant expression vector is a plasmid derived from the pJAM2 plasmid (e.g. pJAM21). The invention also encompasses the pJAM2 and pJAM21 plasmids, as well as recombinant host cells transformed with the pJAM2 and pJAM21 plasmids. A recombinant host cell transformed with pJAM21 has been deposited at Collection Nationale de Cultures de Micro-organisms (CNCM) in Paris, France, on Jun. 23, 1998, under accession number I-2042.

Another aspect of this invention relates to molecules that have been screened according to the methods of this invention and identified as having antibiotic activity against mycobacteria.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with description, serve to explain the principles of the invention.

Figure 1:
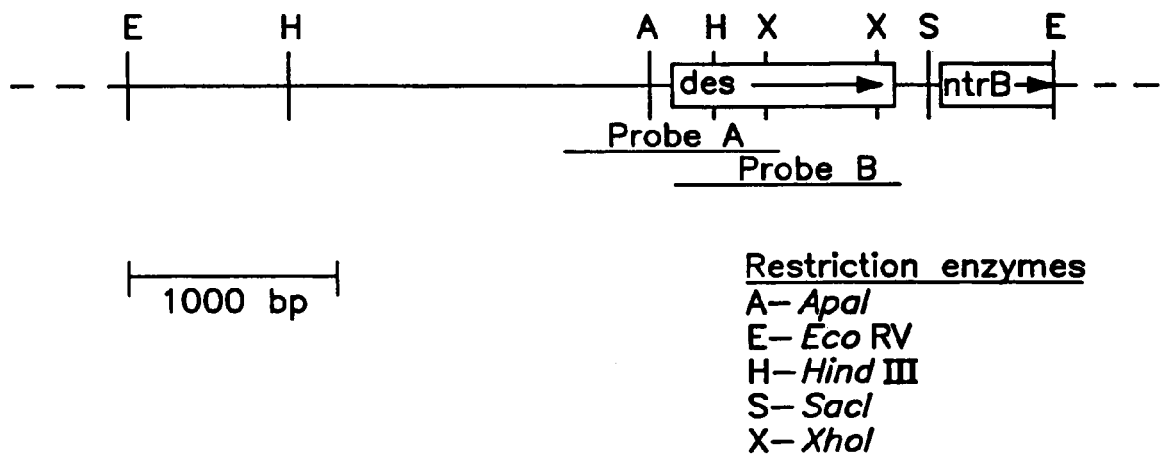
FIG. 1 is a restriction map of the 4.5 kb EcoRV fragment encoding the *M. tuberculosis* des gene.

Sonicated extracts of *E. coli* expressing the DES protein were assayed for Δ9 desaturating activity according to the method described by (Legrand and Bensadoun, 1991), using (stearoyl-CoA) $^{14}C$ as a substrate. However, no Δ9 desaturating activity could be detected. This result is probably linked to the fact that desaturation systems are multi-enzyme complexes involving electron transport chains and numerous cofactors, often difficult to render functional in vitro. Since *E. coli* and mycobacteria are very different from a lipid metabolism point of view, in *E. coli*, the *M. tuberculosis* recombinant Δ9 desaturase might not dispose of all the cofactors and associated enzymes required for activity or might not interact properly with them. Moreover, not all cofactors involved in the Δ9 desaturation process of mycobacteria are known, and they might be missing in the incubation medium.

However, if the DES protein encodes a Δ9 desaturase, an interesting point concerns its primary sequence. Indeed, all animal, fungal, and the only two bacterial Δ9 desaturases sequenced to date (Sakamoto et al., 1994) are integral membrane proteins which have been classified into a third class of diiron-oxo proteins on the basis of their primary sequences involving conserved histidine residues (Shanklin et al., 1994). The plant soluble Δ9 desaturases are the only desaturases to possess the type of primary sequence of class II diiron-oxo proteins (Shanklin & Somerville, 1991). No bacteria have yet been found which have a plant type Δ9 desaturase.

As shown by immunoblotting and ELISA experiments, the DES protein is a highly immunogenic antigen which elicits a B-cell response in 100% of the tuberculosis *M. bovis* or *M. tuberculosis*-infected human patients tested, independently of the form of the disease (extrapulmonary or pulmonary). It also elicits an antibody response in lepromatous leprosy patients. Interestingly, although more sera would need to be tested, tuberculous cattle do not seem to recognize the DES antigen. Furthermore, the ELISA experiments showed that it is possible to distinguish tuberculosis patients from patients suffering from other pathologies on the basis of the sensitivity of their antibody response to the DES antigen. The DES antigen is therefore a good candidate to be used for serodiagnosis of tuberculosis in human patients. Non-tuberculous patients may recognize the DES protein at a low level because they are all. BCG-vaccinated individuals (BCG expressing the protein), or because of cross-reactivity of their antibody response with other bacterial antigens. It would now be interesting to know whether the DES antigen possesses in addition to its B-cell epitopes, T-cell epitopes, which are the only protective epitopes in the host immunological response against pathogenic mycobacteria. If the DES protein is also a good stimulator of the T-cell response in a majority of tuberculosis patients, it could be used either individually or as part of a cocktail of antigens in the design of a subunit vaccine against tuberculosis.

To gain insights into the precise function of this atypical bacterial enzyme, we attempted to interrupt the des gene in the vaccine strain *M. bovis* BCG by allelic exchange. In a first experiment, no allelic exchange mutants were obtained, suggesting that the des gene is essential to the viability of mycobacteria. To investigate this hypothesis, the first experiment was repeated using a *M. bovis* BCG strain transformed with a second wild-type copy of the des gene. Using this transformed *M. bovis* BCG strain, we obtained allelic exchange mutants, in which a wild-type copy of the des gene was replaced by an inactivated copy of the des gene. Thus, allelic exchange was only possible if a second copy of the wild-type des gene had been inserted into the *M. bovis* BCG chromosome. This result strongly suggests that des is an essential gene in mycobacteria from the *M. tuberculosis* complex.

Coupled with the localization of DES at the surface of the tubercle bacilli, and its structural originality (this enzyme's structure differs from all the mammalian and bacterial desaturase structures identified to date), the results of these experiments suggest that the DES protein could be a target for designing new anti-mycobacterial drugs.

Fundamental to the analysis of the biological function and immunological relevance of mycobacterial proteins is their production in a recombinant form that resembles that of their native counterpart. Recent studies analyzing both structure (Garbe et al., 1993; Triccas et al., 1996) and immunogenicity (Garbe et al., 1993; Roche et al., 1996; Triccas et al., 1996) of recombinant proteins obtained from fast growing mycobacterial hosts, such as *Mycobacterium smegmatis*, have demonstrated superiority over the same protein purified from *E. coli* expression systems. Although such approaches for the production of recombinant mycobacterial proteins appear advantageous, two major obstacles lie in the way of further improvement to these systems. The first is the inability to regulate high-level expression of foreign genes in *M. smegmatis*, analogous to systems such as induction of the lac promoter in *E. coli* (de Boer et al., 1983). Secondly, no simple, efficient and widely adaptable method for the purification of proteins from recombinant mycobacteria has been described.

In this application, we attempt to resolve these two problems. First, we describe the construction of a vector, pJAM2, that utilizes the promoter of the inducible acetamidase enzyme of *M. smegmatis* to drive high-level expression of foreign genes in *M. smegmatis*. The 47 kDa acetamidase enzyme of *M. smegmatis* NCTC 8159 permits the growth of the organism on simple amides as the sole carbon source and is highly inducible in the presence of acetamide (Mahenthiralingam et al., 1993). This property has been previously used to assess luciferase as a reporter of gene expression in mycobacteria (Gordon et al., 1994) and to develop a mycobacterial-conditional antisense mutagenesis system (Parish et al., 1997b). In this study, we constructed a vector that allows for regulated high-level expression of foreign genes in mycobacteria by virtue of the *M. smegmatis* acetamidase promoter.

Recombinant *M. leprae* 35 kDa antigen produced in this system represented approximately 8.6% of the total *M. smegmatis* soluble protein, with the amount of protein produced greater than that when the same gene is placed under the control of the strong. mutated β-lactamase promoter of *M. fortuitum* (FIG. 3).

Secondly, we demonstrate the simple and efficient purification of the encoded antigens by use of a poly-histidine tag and one step $Ni^{++}$ affinity chromatography. The addition of the histidine tag did not appear to affect the conformation or immunogenicity of the recombinant protein, suggesting the system described may be extremely useful for the purification of structurally and immunologically intact recombinant mycobacterial proteins from fast-growing mycobacterial hosts.

Figure 12:
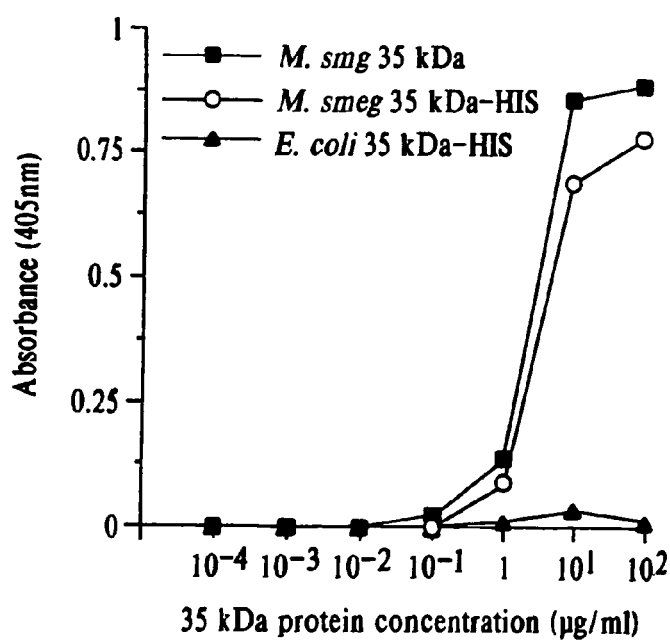
Figure 13:
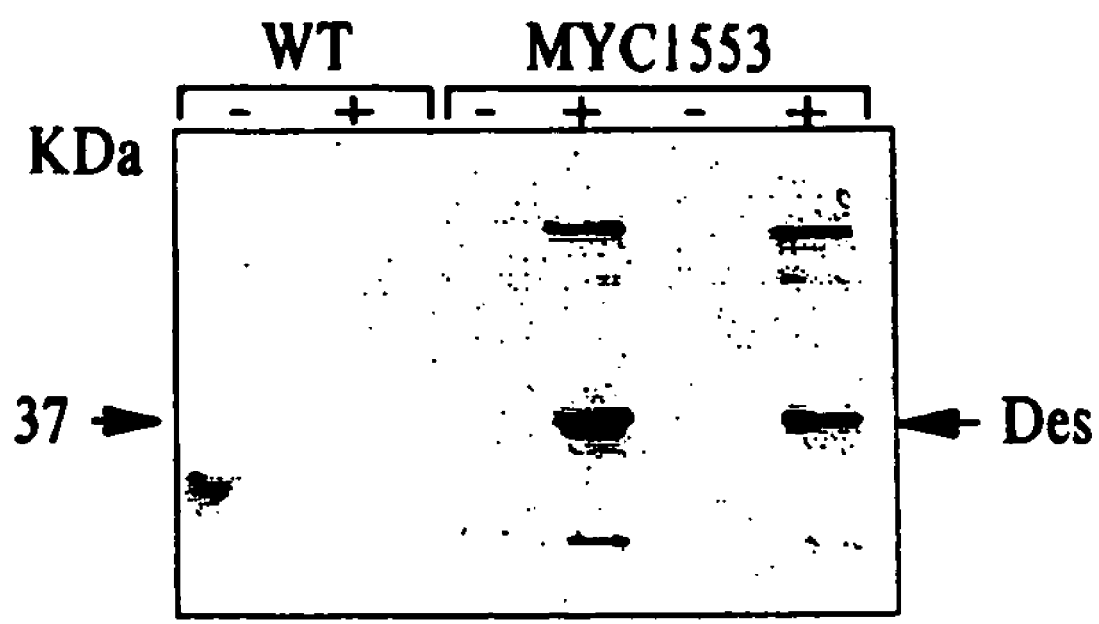

The ability to produce recombinant products in a form that closely resembles their native state is important in the study of microbial antigens and enzymes. Recent studies have highlighted the superiority of recombinant protein purified from mycobacterial hosts compared to *E. coli*-derived products, as assessed by structural and immunological analysis. (Garbe et al., 1993; Roche et al., 1996; Triccas et al., 1996). Previously we have demonstrated that sera from leprosy patients would only recognize the *M. leprae* 35 kDa protein if the antigen was produced in a form that resembles the native protein, based on the binding of conformational dependent mAbs and FPLC size exclusion analysis (Triccas et al., 1996). We reconfirm such a finding with protein produced using the acetamidase promoter expression system (FIG. 12). Furthermore, the addition of 6 histidine residues to the C-terminus of the recombinant protein does not appear to affect its conformation, as there is little difference in the recognition of leprosy sera by histidine-tagged and nonhistidine-tagged 35 kDa protein (FIG. 12). The efficient expression of the 6-histidine tag in mycobacteria and the simple and effective purification of our model protein by Ni-NTA affinity chromatography (FIG. 10) suggest that this versatile purification system, used successfully in a number of eucaryotic and procaryotic expression systems (Crowe et al., 1994), could be more widely applied to mycobacterial proteins. Furthermore, the histidine purification system overcomes the problems, involved with antibody affinity chromatography used in a number of studies to purify recombinant mycobacterial proteins (Roche et al., 1996; Triccas et al., 1996), such as the unavailability of appropriate antibodies or the presence of homologues capable of binding the antibody. Together, these results suggest an application for the pJAM2 expression vector in the production of native-like recombinant mycobacterial proteins that can be exploited to correctly analyze protein function and antigenicity.

The invention will be further clarified by the following examples, which are intended to be purely exemplary of the invention.

EXAMPLES

Bacteria, Media and Growth Conditions

The bacterial strains and plasmids used in this study are listed in FIG. 8. *E. coli* DH5a or BL21 (DE3) pLysS cultures were routinely grown in Luria B medium (Difco) at 37° C. *Mycobacterium* cultures were grown in Middlebrook 7H9 medium (Difco) supplemented with Tween 0.05%, glycerol (0.2%) and ADC (glucose, 0.2%; BSA fraction V, 0.5%; and NaCl, 0.085%) at 37° C. When required, antibiotics were added at the following concentrations: ampicillin (100 µg/ml), kanamycin (20 µg/ml).

Human and Cattle Sera

Serum specimens from 20 individuals with pulmonary or extra-pulmonary tuberculosis (*M. tuberculosis* infected) were obtained from the Bligny sanatorium (France). Six sera from *M. bovis* infected human tuberculous patients and 24 sera from BCG-vaccinated patients suffering from other pathologies were respectively obtained from Institut Pasteur, (Madagascar), and the Centre de Biologie Médicale spécialisée (CBMS) (Institut Pasteur, Paris). Sera from tuberculous cattle (*M. bovis* infected) were obtained from CNEVA, (Maison Alfort).

Subcloning Procedures

Restriction enzymes and T4 DNA ligase were purchased from Gibco/BRL, Boehringer Mannheim and New England Biolabs. All enzymes were used in accordance with the manufacturer's recommendations. A 1-kb ladder of DNA molecular mass markers was from Gibco/BRL. DNA fragments used in the cloning procedures were gel purified using the Geneclean II kit (BIO 101 Inc., La Jolla, Calif.). Cosmids and plasmids were isolated by alkaline lysis (Sambrook et al., 1989). Bacterial strains were transformed by electroporation using the Gene Pulser unit (Bio-Rad Laboratories, Richmond, Calif.).

Southern Blot Analysis and Colony Hybridization

DNA fragments for radiolabeling were separated on 0.7% agarose gels (Gibco BRL) in a Tris-borate-EDTA buffer system (Sambrook et al., 1989) and isolated from the gel by using Geneclean II (BIO 101). Radiolabeling was carried out with the random primed labeling kit Megaprime (Amersham) with 5 µCi of ($\alpha$-$^{32}$P)dCTP, and unincorporated label was removed by passing through a Nick Column (Pharmacia). Southern blotting was carried out in 0.4 M NaOH with nylon membranes (Hybond-N+, Amersham) according to the Southern technique (Southern, 1975), prehybridization and hybridization was carried out as recommended by the manufacturer using RHB buffer (Amersham). Washing at 65° C. was as follows: two washes with 2×SSPE (150 mM NaCl, 8.8 mM NaH$_2$PO$_4$, 1 mM EDTA pH 7.4)-SDS 0.1% of 15 minutes each, one wash with 1×SSPE-SES 0.1% for 10 minutes, two washes with 0.7×SSPE-SDS 0.1% of 15 minutes each. Autoradiographs were prepared by exposure with X-ray film (Kodak X-OMAT) at −80° C. overnight. Colony hybridization was carried out using nylon membrane disc (Hybond-N+ 0.45 µm, Amersham). *E. coli* colonies adsorbed on the membranes were lysed in a (0.5M NaOH, 1.5M NaCl) solution, before being placed for one minute in a microwave oven to fix the DNA. Hybridization and washes were described for the Southern blotting analysis.

DNA Sequencing and Analysis

Sequences of double-stranded plasmid DNA were determined by the dideoxy-chain termination method (Sanger et al., 1977) using the Taq Dye Deoxy Terminator Cycle sequencing Kit (Applied Biosystems), on a GeneAmp PCR System 9600 (Perkin Elmer), and run on a DNA Analysis System-Model 373 stretch (Applied Biosystems). The sequence was assembled and processed using DNA strider™ (CEA, France) and the University of Wisconsin Genetics Computer Group *UWGCG) packages. The BLAST algorithm (Altschul et al., 1990) was used to search protein data bases for similarity.

Expression and Purification of the DES Protein in *E. coli*

A 1043 bp NdeI-BamHI fragment of the des gene was amplified by PCR using nucleotides JD8:

(5'-CGGCATATGTCAGCCAAGCTGACCGAC-CTGCAG-3') (SEQ ID NO:1), and JD9:

(5'CCGGGATCCCGCGCTCGCCGCTCTGCATCGTCG-3') (SEQ ID NO:2), and cloned into the NdeI-BamHI sites of pET14b (Novagen) to generate pET-des. PCR amplifications were carried out in a DNA thermal Cycler (Perkin Elmer), using Taq polymerase (Cetus) according to the manufacturer's recommendations. PCR consisted of one cycle of denaturation (95° C., 6 min) followed by 25 cycles of amplification consisting of denaturation (95° C., 1 min), annealing (57° C., 1 min), and primer extension (72° C., 1 min). In the pET-des vector, the expression of the des gene is under control of the T7 bacteriophage promoter and the DES antigen is expressed as a fusion protein containing six histidine residues. Expression of the des gene was induced by addition of 0.4 mM IPTG in the culture medium. The DES protein was purified by using a nickel-chelate affinity resin according to the recommendations of the supplier (Qiagen, Chatsworth, Calif.)

SDS-PAGE and Immunoblotting

Sodium dodecyl sulfate-polyacrylamide gel electrophoresis (SDS-PAGE) was carried out as described by (Laemmli, 1970). For Western blotting experiments (immunoblotting), approximately 10 μg of DES purified protein were run on a SDS-polyacrylamide gel and transferred on nitrocellulose membranes (Hybond C extra, Amersham) using a Bio-Rad mini transblot apparatus according to the recommendations of the manufacturer (Bio-Rad Laboratories, Richmond, Calif.). Transfer yield was visualized by transient staining with Ponceau Rouge. The membrane were incubated with human patient or cattle sera diluted 1/200 at 37° C. for 1 hour and with a goat anti-human (Promega) or rabbit anti-cattle (Biosys) IgG alkaline phosphatase-conjugated secondary antibody diluted 1/2500' for 30 minutes at 37° C. The color reaction was performed by addition of 5-bromo-4-chloro-3-indolylphosphate (0.165 mg/ml) and toluidinum nitroblue tetrazolium (0.33 mg/ml) as substrates.

ELISA

The human or cattle sera were tested for antibodies against DES by enzyme-linked immunosorbent assay (ELISA). The 96-well micro-titer trays (Nunc, Rochester, N.Y.) were coated with 0.1 μg (per well) of purified DES protein in guanidine hydrochloride buffer A (6 M guanidine hydrochloride, 0.1 M $NaH_2PO_4$, 0.01 M Tris, pH 8) (1 h at 37° C. and 16 h at 4° C.). After three washes, wells were saturated with bovine serum albumin 3% in phosphate buffered saline (PBS) for 30 min. at room temperature. After three washes, sera diluted from 1/50° to 1/3200° in buffer (PBS, 0.1% Tween 20, 1% bovine serum albumin) were added to the wells for 2h at 37° C. After three washes, the wells were treated with goat anti-human IgG-alkaline phosphatase conjugate (Promega, Madison, Wis.) diluted 1/4000° for 1 h at 37° C. Then, 4 mg of p-nitrophenylphospate per ml were added as substrate. After 20 minutes of incubation at 37° C., the plates were read photometrically at an optical density of 405 nm in micro-ELISA Autoreader (Dynatech, Marnes la Coquette, France).

Statistics

Antibody responses of the different sera tested were compared by using the Student t test. $P \geq 0.05$ was considered nonsignificant.

Nucleotide Sequence and Accession Number

The nucleotide sequences of des has been deposited in the Genome Sequence Data Base (GSDB) under the accession number U49839.

Cloning of the des Gene

The construction of a fusion library of *M. tuberculosis* genomic DNA to the phoA gene and its expression in *M. smegmatis*, described by (Lim et al., 1995), led to the isolation of several PhoA⁺ clones. pExp421 is the plasmid harbored by one of the $PhoA^+$ clones selected from this library. Detection of enzymatically active alkaline phosphatase indicated that the pExp421 insert contains functional expression and exportation signals. Restriction analysis showed that pExp421 carries a 1.1 kb insert. Partial determination of its sequence identified a 577 bp ORF, named des, fused in frame to the phoA gene and presenting two motifs, of 9 and 14 amino acids, conserved with soluble stearoyl-acyl-carrier protein desaturases (Lim et al., 1995).

To isolate the full-length des gene, the *M. tuberculosis* H37Rv pYUB18 genomic cosmid library (Jacobs et al., 1991), was screened by colony hybridization with the 1.1 kb probe (probe A, see FIG. 1). Two hybridizing cosmids named $C_3$ and $C_4$ were selected for further isolation of the gene. $C_3$ and $C_4$ were cut with several restriction enzymes and subjected to Southern blot analysis using the 1.1 kb fragment as a probe.

The EcoRV restriction profile revealed a single hybridizing fragment of 4.5 kb which was subcloned into pBluescript $KS^-$ (Stratagene, La Jolla, Calif.) to give plasmid pDS-des.

Characterization of the des Gene

The DNA sequence of the full des ORF was determined (FIG. 7). The des gene was shown to cover a 1017 bp region, encoding a 339 amino acid protein with a calculated molecular mass of 37 kDa. The ORF starts with a potential ATG start codon at position 549, and ends with a TAG stop codon at position 1565. There is a potential Shine-Delgarno motif (GGAGG) at position −8 upstream of the ATG. The G+C content of the ORF (62%) is consistent with the global GC content observed in the mycobacterial genome. The nucleotide and deduced amino acid sequences of the des gene were compared to sequences in databases. They showed very high homologies to the *M. leprae* aadX gene located on cosmid B2266, deposited in GenBank as part of the *M. leprae* genome sequencing project (GenBank accession number n°. U15182). Within the coding region, the DNA sequences were 79% identical while the encoded proteins were 80% identical (88% including conserved residues). The des gene also scored significantly against soluble stearoyl-ACP desaturases: 44% identity at the nucleotide level, 30% identity (51% including conserved residues) at the amino acid level, to the *Oryza saliva* stearoyl-ACP desaturase (accession n°. D38753).

Although the detection of phoA enzymatic activity in the *M. smegmatis* clone harboring the pEXp421 suggests the DES protein is exported, no structural similarities were found between the DES protein N terminal amino acids and signal sequences of bacterial exported proteins (Izard & Kendall, 1994).

As in the *M. leprae* genome, a second ORF presenting high homologies of the *M. leprae* putative NtrB gene (cosmid B2266), is located downstream of the des gene in *M. tuberculosis*. Interestingly, the two ORF, des and Ntrb, are separated in *M. tuberculosis* by two direct repeats of 66 nucleotides overlapping on 9 nucleotides (FIG. 2).

The DES Protein Presents the Conserved Amino Acid Motifs of the Class II Diiron-oxo Proteins Further analysis of the amino acid sequence of the DES protein revealed the presence of conserved motifs found only in class II diiron-oxo proteins (Fox et al., 1994) (FIG. 3). These proteins are oxo-bridged diiron clusters (Fe—O—Fe) containing proteins. They possess in their secondary structure 4 alpha helices involved in the protein-derived cluster ligands. As revealed by X-ray structure studies, in these proteins, the diiron axis is oriented parallel to the long axis of the four helix bundle with ligands arising from four noncontiguous helices, B, C, E and F. *M. tuberculosis* DES protein appears to have the same active site residues as the class II diiron-oxo enzymes. This includes Glu and His residues ($E_{107}$ and $H_{110}$ in helix C, $E_{167}$ in helix E and $E_{197}$ and $H_{200}$ in helix F) that are ligands to the iron atoms, Asp, Glu and Arg residues ($E_{106}$ and $R_{109}$ in helix C, $D_{196}$ in helix F) that are involved in a hydrogen-bonding network to the cluster and, Ile and Thr residues that may be part of the $O_2$-binding site ($T_{170}$ in helix E, $I_{193}$ in helix F). Thus, the *M. tuberculosis* DES protein contains in its primary sequence a conserved EEXXH (SEQ ID NO:3) motif and a conserved DEXXH (SEQ ID NO:4) motif, where X represents any amino acid. The conserved motifs are separated by 85 amino acids.

The class II diiron-oxo protein family contains up to date ribonucleotide reductases, hydrocarbon hydroxylases (methane mono-oxygenase, toluene-4-mono-oxygenase and phenol hydroxylase) and soluble-ACP desaturases. On the overall sequence alignment the DES protein presents higher homology to soluble stearoyl-ACP desaturases than to ribonucleotide reductases or bacterial hydroxylases. The percentage identity at the amino acid level of the DES protein was said to be 30% with the *Oryza sativa* stearoyl-ACP desaturases, whereas it is only 17% with the *Methylococcus capsulatus* methane mono-oxygenase (accession n°. M60276) and 17.7% with the Epstein Barr ribonucleotide reductase (accession n°. V01555). Homologies to the soluble Δ9 desaturases mostly concern the amino acids located within the active site in helices C, E, and F (FIG. 3).

The method according to the invention can be carried out for the screening and selection of molecules interacting with the enzymatic activity of DES protein, for example, for acyl-ACP desaturase normally produced by higher plants.

The DES Protein Shares Structural Features with the Plant Acyl-ACP Desaturases

The three-dimensional structure of the DES protein was modeled based on homology with the *Ricinus communis* Δ9 stearoyl-ACP desaturase. The structure of this plant desaturase was determined by protein crystallography to 2.4 Å resolution (Lindqvist et al., 1996). The model obtained has no Ramachandran outliers, has an excellent stereochemistry for both main chain and side chains and has no bad contacts.

302 residues out of the 337 total residues of the *M. tuberculosis* enzyme could be built based on the template's structure and aligned with an r.m.s. of 0.34 Å for their Cα atoms. These 302 DES residues share 26% sequence identity with the residues of plant Δ9 stearoyl-ACP desaturase. Thus, the structures of these 302 residues in the model represent a good approximation of their true structure.

Figure 3B:
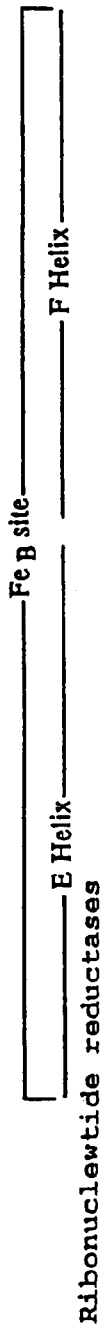

The plant Δ9 stearoyl-ACP desaturase and DES protein share almost complete sequence identity in the areas encoding the four helices, which include the ligands for the bi-nuclear iron center, as well as in the surrounding areas and in the area around the catalytic site. Therefore, one can be confident with the structure of the residues located within these areas that share substantial amino acid identity. (FIGS. 3a and 3b). These areas include the part of the fatty acid binding site which is close to the active site. From the structure of the Δ9 stearoyl-ACP desaturase it was concluded that the fatty acid part of the substrate is completely buried in the enzyme, in a deep hydrophobic channel, positioning the site of desaturation between carbon 9 and 10 in the area of the active site close to the binuclear iron center. (Lindqvist et al., 1996). The shape of the channel forces the substrate to bind in a confirmation close to the product's cis-configuration. From amino acid sequence comparisons of plant desaturases it was further concluded that the size of the amino acid side chains at the bottom of this channel determines the chain length beyond the point of double bond insertion that can be accepted by the various plant enzymes. (Cahoon et al., 1997). In the DES protein, the active site is completely conserved, suggesting that DES is evolutionarily related to the plant desaturases. If DES catalyzes a desaturation reaction, judging from the conserved shape of the substrate's pocket, the product of the enzymatic reaction would have a cis-configuration around the introduced double bond. Inspection of the bottom of the substrate channel in the model of the DES protein shows that the exchange of threonine T181 in the plant Δ9 stearoyl-ACP desaturase for the bulkier glutamine in DES (Q145) has shortened the pocket significantly. This implies that the substrate in DES would have a maximum of seven carbons beyond the point of double bond insertion as compared to nine carbons in the plant stearoyl-ACP desaturase. Also, the replacement of methionine M114 in the plant enzyme by a negatively charged glutamic acid in DES (E85) could indicate that the substrate for the Des protein carries a polar or even positively charged group that can interact with this sidechain. Alternatively, the polarity could make it difficult for hydrophobic fatty acid tails to reach the bottom of the already shorter cavity, thereby further limiting the number of possible carbons beyond the point of double bond insertion (e.g., to five carbons). Other amino-acid substitutions in the binding cleft do not affect the nature, shape and size of the substrate's binding cavity.

The electrostatic potential surface of the Δ9 stearoyl-ACP desaturase and of the DES protein around the entrance of the substrate's binding channel are very different. This difference indicates that the DES protein and the plant Δ9 stearoyl-ACP desaturase may require different associated cofactors for activity and, in particular, different forms of fatty acid substrates.

Distribution of the des Gene in other Mycobacterial Species

Figure 4:
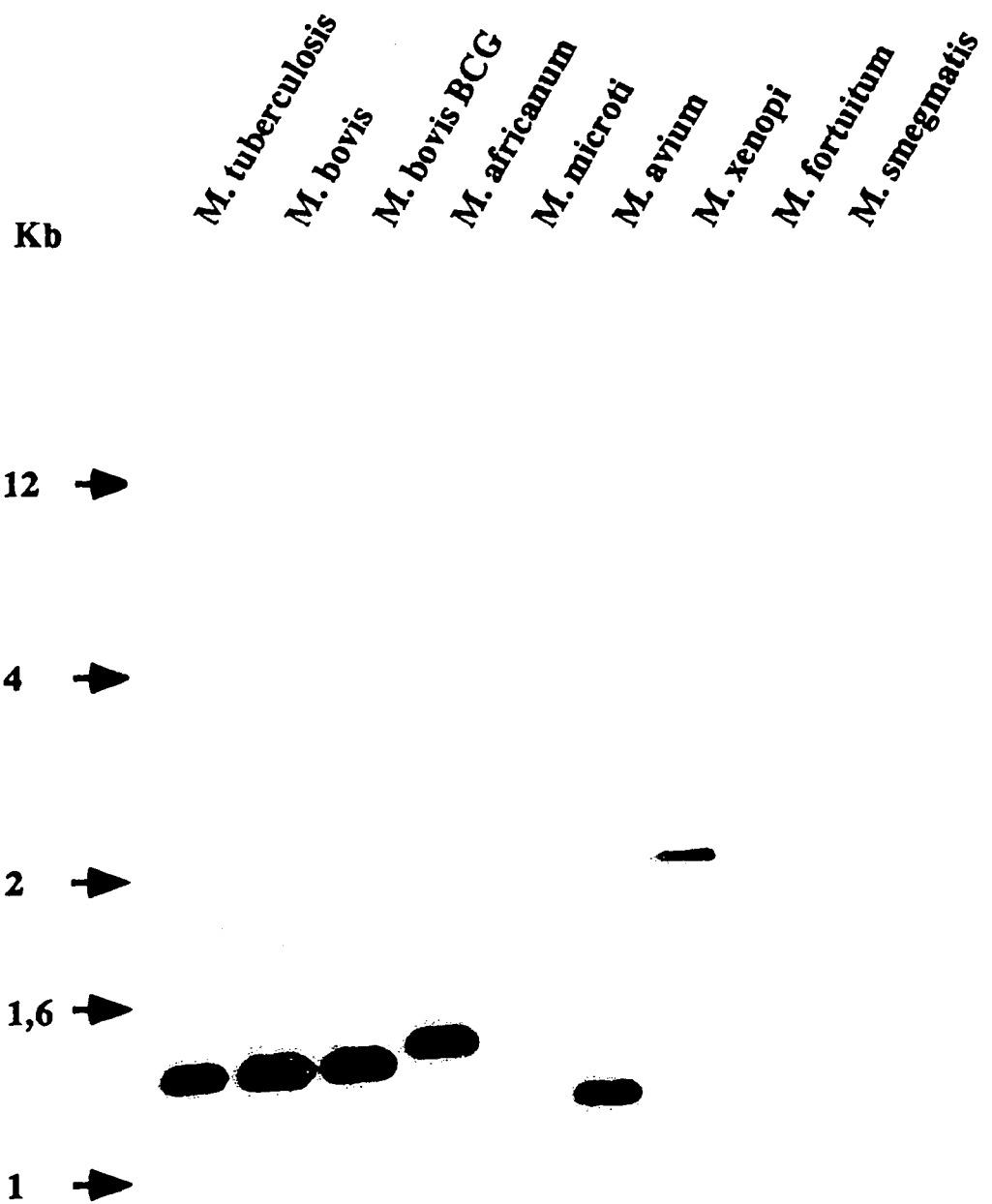

The presence of the des gene in PstI-digested chromosomal DNA from various mycobacterial strains was analyzed by Southern blotting (FIG. 4). The probe used (probe B) is a PCR amplification product corresponding to nucleotides 572 to 1589 (see FIG. 1). The probe hybridized on all mycobacterial genomic DNA tested. Strong signals were detected in *M. tuberculosis, M. bovis, M. bovis* BCG, *M. Africanum* and *M. avium*. Weaker signals were visible in *M. microti, M. xenopi, M. fortuitum* and *M. smegmatis*. Thus, the des gene seems to be present in single copy at least in the slow growing *M. tuberculosis, M. bovis, M. bovis* BCG, *M. africanum, M. avium* and *M. xenopi* as well as in the fast growing *M. smegmatis*.

Expression of the des Gene in *E. coli*

Figure 5:
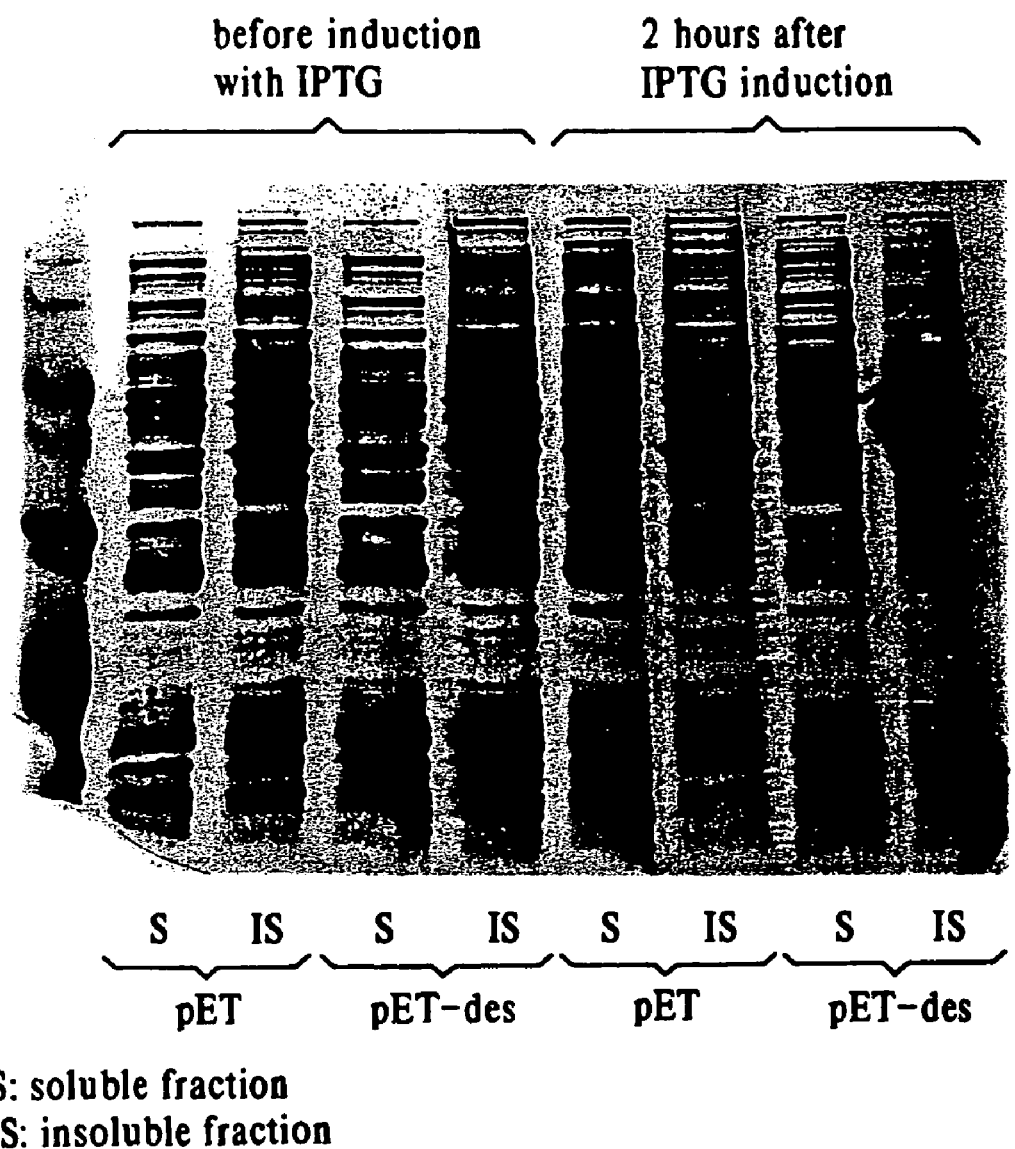

In order to over express the DES protein, the des gene was subcloned into the bacteriophage T7 promoter-based expression vector pET14b (Novagen). A PCR amplification product of the des gene (see material and methods) was cloned into the NdeI-BamHI sites of the vector, leading to the plasmid pET-des. Upon IPTG induction of *E. coli* BL21 DE3 pLysS cells harboring the plasmid pET-des, a protein of about 40 kDa was overproduced. The 40 kDa size of the overproduced protein corresponds with the molecular mass calculated from the deduced polypeptide. As shown in FIG. 5, the great majority of the overproduced DES protein is present in the insoluble matter of *E. coli* cells. This probably results from the precipitation of the over-concentrated protein in *E. coli* cytoplasm resulting in the formation of inclusion bodies. To be able to dissolve the protein, the purification was carried out using a nickel chelate affinity resin underdenaturing conditions in guanidine hydrochloride buffers. Among all the conditions tested (pH, detergents, etc.), the only condition in which the protein could be eluted without precipitating in the column and remain soluble, was in a buffer containing 6 M guanidine hydrochloride.

Immunogenicity of the DES Protein after Infection

Figure 9:
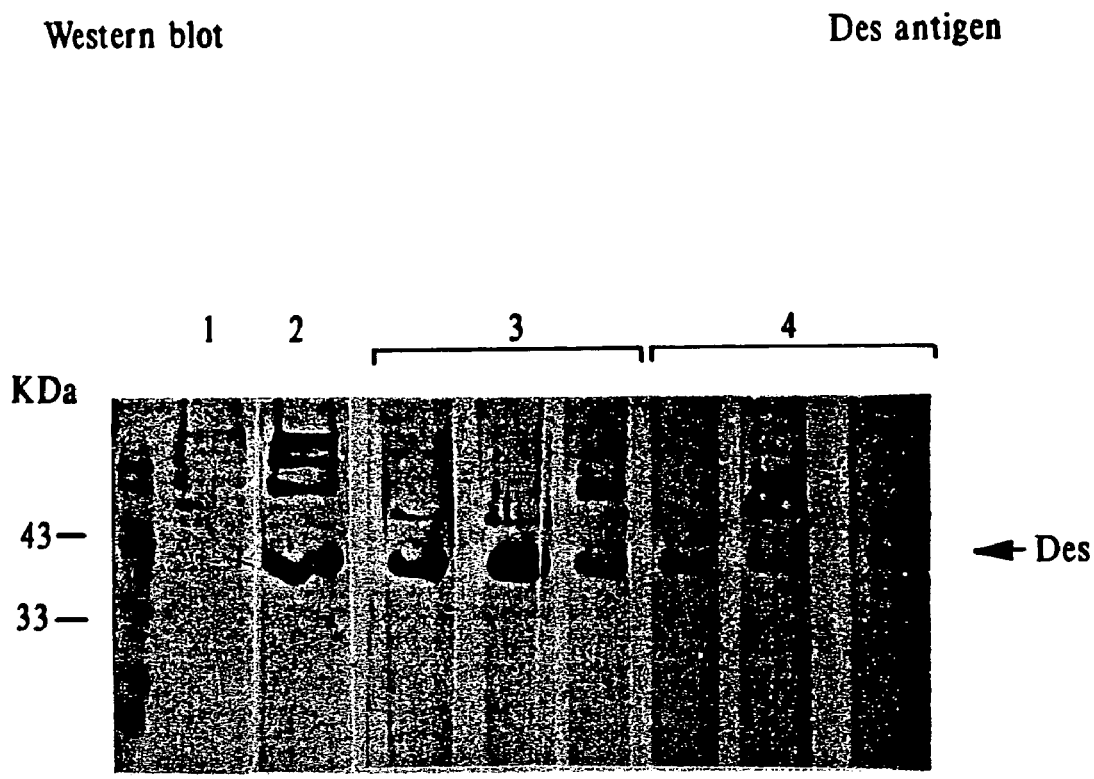

Twenty serum samples from *M. tuberculosis* infected human patients (4 with extra-pulmonary tuberculosis, 15 with pulmonary tuberculosis and 1 with both forms of the disease), 6 sera from *M. bovis* infected human patients and 4 sera from *M. bovis* infected cattle were tested either pooled or taken individually in immunoblot experiments to determine the frequency of recognition of the purified DES protein by antibodies from infected humans or cattle. 20 out of the 20 sera from the *M. tuberculosis* infected human patients and 6 out of the 6 sera from the *M. bovis* infected human patients recognized the recombinant antigen as shown by the reaction with the 37 kDa band, (FIG. 9). Furthermore, a pool of sera from human lepromatous leprosy patients also reacted against the DES antigen.

In contrast, the pool of serum specimens from *M. bovis* infected cattle did not recognize the DES protein. These results indicate that the DES protein is highly immunogenic in tuberculosis human patients. Both pulmonary and extra-pulmonary, tuberculosis patients recognize the antigen.

Magnitude of Human Patients' Antibody Responses

Figure 6:
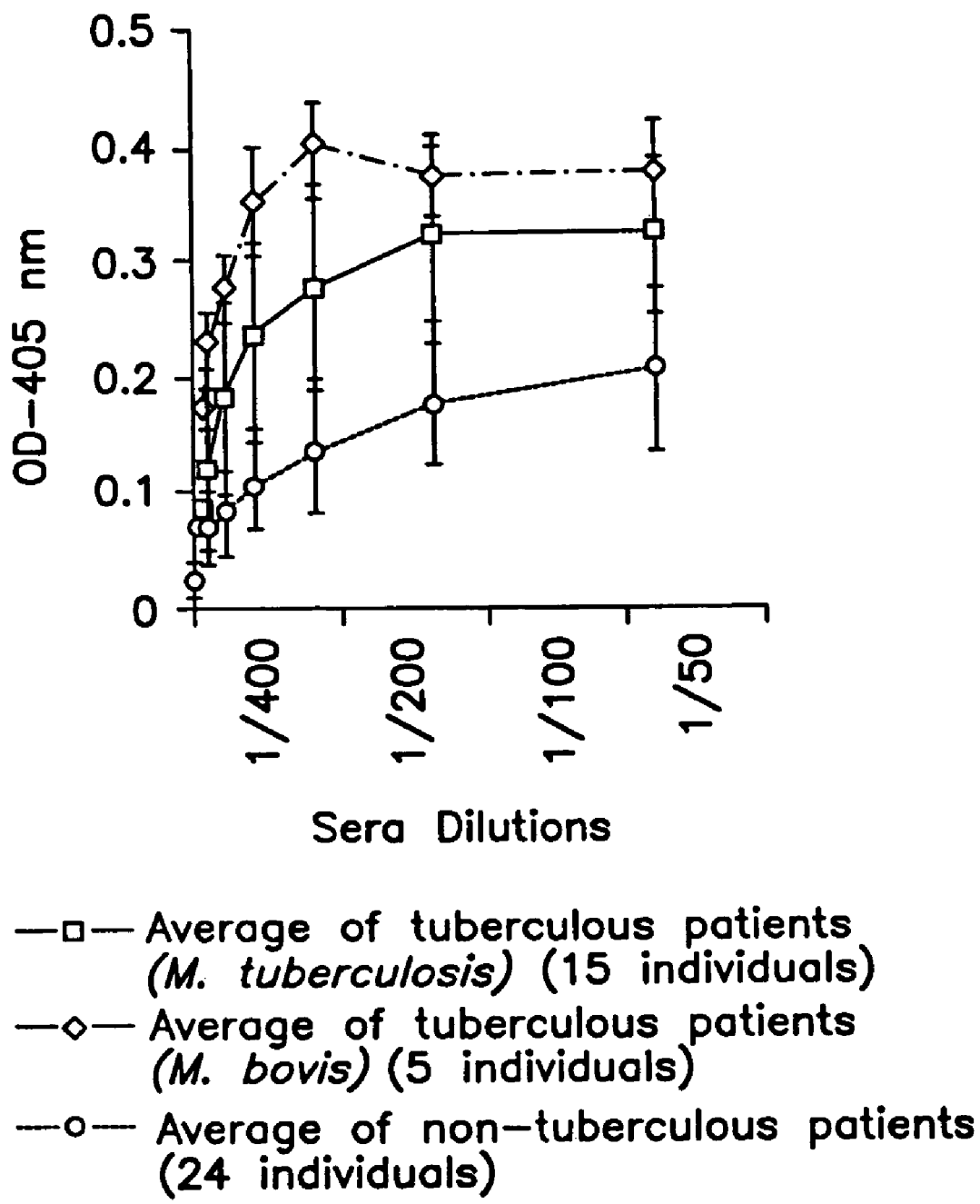

An enzyme-linked immunosorbent assay (ELISA) was used to compare the sensitivity of the different serum samples from 20 tuberculosis patients (15 infected by *M. tuberculosis* and 5 infected by *M. Bovis*) to the DES antigen. This technique was also carried out to compare the sensitivity of the antibody response to DES of the 20 tuberculosis patients to the antibody response of 24 patients (BCG-vaccinated) suffering from other pathologies. As shown in FIG. 6, patients suffering from pathologies other than tuberculosis, react at low level to the DES antigen (average $OD_{405}=0.17$ for a serum dilution $1/100^4$) The average antibody response from the tuberculosis patients infected by *M. tuberculosis* or *M. bovis* against the same antigen is much more sensitive ($OD_{405}=0.32$ and $OD_{405}=0.36$ respectively, for a serum dilution $1/100^4$). This difference in the sensitivity, of the immunological response is statistically highly significant at every dilution from $1/50^a$ to $1/3200^a$ as shown by a Student $I_{95}$ test ($I_{95}$=5.18, 6.57, 6.16, 5.79, 4.43, 2.53 and 1.95, at sera dilutions $1/50^a$, $1/100^a$, $1/200^a$, $1/400^a$, $1/800^a$, $1/600^a$ and $1/3200^a$, respectively). No differences in the sensitivity of the antibody response was noticed between patients suffering from pulmonary or extra-pulmonary tuberculosis.

Allelic Exchange of des Gene

We constructed an inactivated copy of the des gene by inserting into the XhoI site of the ApaI/SacI restriction fragment carrying the des gene (Jackson et al., 1997), a kanamycin (Km) resistance cassette. This (des:Km) construct was then inserted, along with the XylE gene, which encodes the *Pseudomonas* catechol dioxygenase conferring upon mycobacteria a yellow color when sprayed with catechol (Pelicic et al., 1997), into the pJQ200 plasmid, a pBluescript-derived *E. coli* vector carrying the sacB gene. The resulting vector was called pJQdKX.

In a first experiment, we transformed *M. bovis* BCG with pJQdKX and tried to select mutants resulting from allelic exchange events inside the des locus by using a two step procedure such as the one described by (Pelicic et al., 1996). In the first step, we selected, on kanamycin-containing medium, a transformant that has integrated the whole vector inside its chromosome by a single crossing-over within the des locus. In the second step, using the counter-selection properties of the sacB gene, we selected bacteria that have undergone a second intrachromosomal crossing-over, resulting in the replacement of the wild type copy of the des gene by its inactivated copy (des:Km), i.e., allelic exchange mutants.

Although at the first step of the procedure, 100% of the transformants resulted from the integration of the pJQdKX vector by a single homologous recombination event, no allelic exchange mutants were obtained after the second selection step. 99.53% of the (Km, Sucrose) resistant colonies obtained at the end of the selection procedure were XylE+, indicating that they still carried the vector in their chromosome and probably also carried mutations in the sacB gene resulting in their sucrose-resistant phenotype. The 0.47% XylE− remaining colonies possibly carried mutations in both the sacB and the XylE genes since genetic analysis (genomic hybridization, PCR) indicated they were not des-allelic exchange mutants. This result suggests that the des gene might be essential to *M. bovis* BCG.

In order to investigate this hypothesis, we performed a second experiment in which we inserted, using an integrative vector pAV6950 (Moniz-Pereira et al., 1995), a second wild type copy of the des gene (carried on a ApaI-SacI restriction fragment; see above) in the chromosome of a *M. bovis* BCG transformant resulting from the first selection step described above. The resulting *M. bovis* BCG thus contained two wild type copies of the des gene in addition to the (des:Km) copy carried by the inserted pJQdKX vector. When the second selection step was applied on a culture of this bacteria, 34% of the (Km-sucrose)-resistant colonies obtained were XylE−. Genetic analysis of these candidates revealed that all of them corresponded to allelic exchange mutants. The other 66% (Km-sucrose)-resistant and XylE+ colonies probably carried mutations in the sacB gene.

Construction of the Acetamidase Promoter Expression Vector pJAM2

The acetamidase promoter region was amplified from plasmid pAMI1, which contains the *M. smegmatis* NCTC 9449 inducible acetamidase gene and upstream region (Mahenthiralingam et al., 1993), by use of primers HIS5:

(CACGGTACCAAGCTTTCTAGCAGA) (SEQ ID NO:38), and HIS7:

(GTCAGTGGTGGTGGTGGTGGTGTCTA-GAAGTACTGGATCCGAAAACTACCTCG) (SEQ ID NO:39). The resulting 1.6 kb fragment was cloned into plasmid pJEM12 (Timm et al., 1994b) to give plasmid pJAM2 (FIG. 2A). The coding region of the *M. leprae* 35 kDa protein was amplified by primers JN8: (TAGCTG-CAGGGATCCATGACGTCGGCT)(SEQ ID NO:40), and 35REV2 (GTGTCTAGACTTGTACTCATG) (SEQ ID NO:41), and cloned into the BamHI/XbaI sites of pJAM2, yielding pJAM4. The gene encoding the *M. tuberculosis* DES antigen was amplified by primers JD17:

(GGGTCTAGAACGACGGCTCATCGCCAGTTTGCC) (SEQ ID NO:42), and JD18:

(CCCGGATCCATGTCAGCCAAGCTGACCGACCTG) (SEQ ID NO:43) and also cloned into the BamHI/XbaI sites of pJAM2 to give plasmid pJAM21.

Expression and Purification of Recombinant Histidine-Tagged Protein from *M. smegmatis*

Plasmids pJAM4 and pJAM21 were introduced into *M. smegmatis* $mc^2155$ and kanamycin resistant colonies grown in M63 medium [$7.6\times10^2$M $(NH4)_2SO_4$, 0.5M $KH_2PO_4$, $5.8\times10^{-6}$M $FeSO_4.7H_2O$, pH 7] supplemented with 2% succinate (Sigma Chemical Co., St Louis, Mo.) for uninduced cultures or 2% succinate and acetamide (Sigma) for induced cultures. Bacteria were grown for 3 days, after which cells were harvested and sonicated 4 times for 1 minute. Sonicates were analyzed for expression of recombinant proteins by SDS-PAGE and immunoblotting with the anti-35 kDa monoclonal antibody (mAb) CS38 for the *M. leprae* 35 kDa protein (CS38 supplied by Professor Patrick Brennan, Colorado State University, Colorado) or for the *M. tuberculosis* DES antigen using an anti-DES murine-derived polyclonal antibody. For protein purification, the sonicates were applied to Ni-NTA resin (Qiagen Inc., Calif.) and bound protein was washed consecutively with 5 mM, 20 mM and 40 mM imidazole (Sigma) in sonication buffer (1×PBS, 5% glycerol, 0.5M NaCl and 5 mM $MgCl_2$). Protein was eluted with 200 mM imidazole in sonication buffer and dialyzed against PBS. Nonhistidine-tagged *M. leprae* 35 kDa protein derived from *M. smegmatis* and the *E. coli* 35 kDa 6-histidine fusion protein were purified as described previously (Triccas et al., 1996).

Protein Capture ELISA

ELISA plates were coated with the murine anti-*M. leprae* 35 kDa mAb ML03 (50 mg/ml; supplied by Professor J. Ivanyi, Hammersmith Hospital, London, UK) and mycobacterial sonicates were added at a concentration range of 0.1 mg/ml to 100 mg/ml. Plates were blocked with 3% bovine serum albumin (BSA), washed, and anti-rabbit 35 kDa protein polyclonal antibody (1:1000) added. Binding was visualized using alkaline phosphatase conjugated anti-rabbit IgG (Sigma) and n-nitro-phenyl-phosphate (NPP) (1 mg/ml). Protein amount was determined by comparison with purified *M. leprae* 35 kDa protein concentration standards (Triccas et al., 1996).

Assessment of Protein Binding to Leprosy Sera by ELISA

Microtitre plates were coated with antigen (100 pg/ml to 100 mg/ml) overnight at room temperature. Plates were washed, blocked with 3% BSA, and pooled sera (diluted 1:100) added for 90 minutes at 37° C. Plates were washed, and alkaline phosphatase conjugated anti-human IgG (Sigma) added for 60 minutes at 37° C. Binding was visualized by the addition of n-nitro-phenyl-phosphate (1 mg/ml) and absorbance was measured at 405 nm.

Construction of the pJAM2 Vector and Utilization for Over-Expression of the Gene Encoding the 35 kDa Antigen of *M. leprae* in *M. smegmatis*

Figures 2A, 2B:
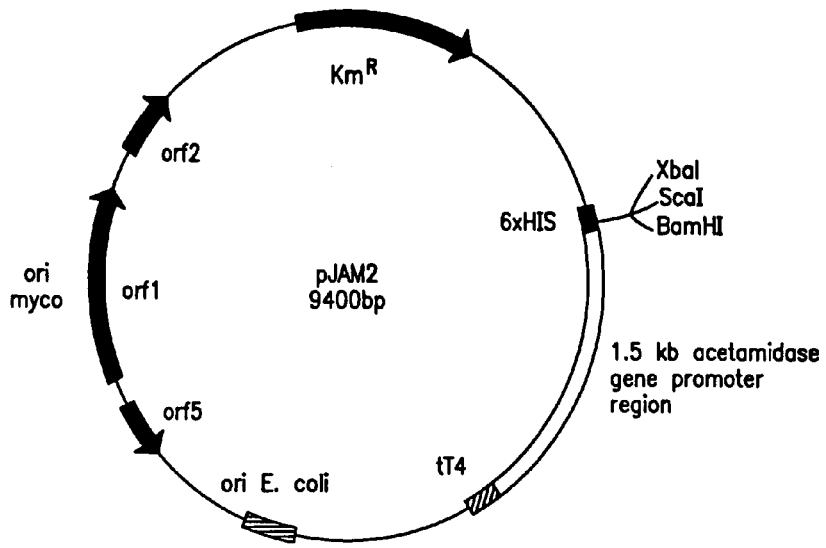
FIG. 2A is a vector map for the pJAM2 plasmid.
FIG. 2B is the nucleotide sequence of the multi-cloning plant stearoyl-ACP-desaturases), catalyzing oxydative desaturation of the CoA derivatives of stearic and palmitic acid to the corresponding Δ9 monounsaturated fatty acids has been biochemically characterized in *Mycobacterium phlei* (Fulco & Bloch, 1962; Fulco & Bloch, 1964; Kashiwabara et al., 1975; Kashiwabara & Sato, 1973). This system was shown to be firmly bound to a membranous structure (Fulco & Bloch, 1964). Thus, *M. tuberculosis* stearoyl-Coenzyme A desaturase (Δ9 desaturase) is expected to be an exported protein.
Figure 10A:
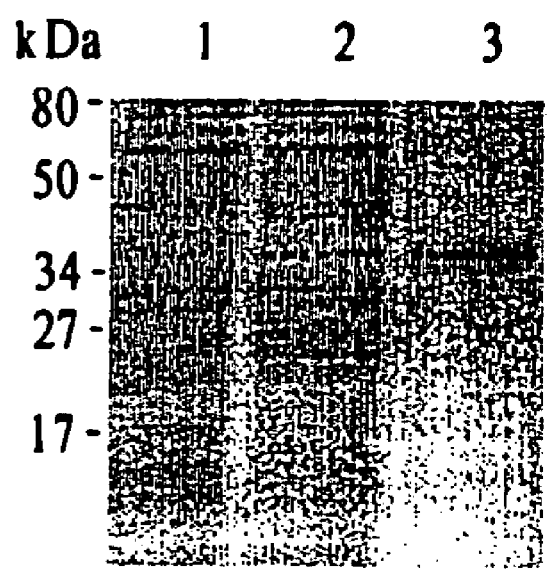
Figure 10B:
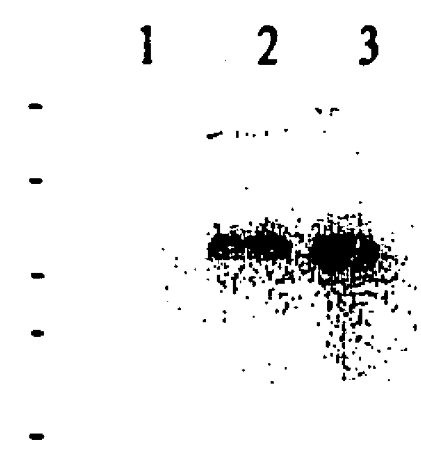

The promoter region of the gene encoding the acetamidase of *M. smegmatis* NCTC 9449 permits the inducible expression of the enzyme in the presence of the substrate acetamide (Mahenthiralingam et al., 1993). In order to determine if the promoter could regulate the expression of foreign genes placed under its control, the vector pJAM2 was constructed (FIG. 2A). This plasmid contains 1.5 kb upstream of the acetamidase coding region, DNA encoding the first 6amino acids of the acetamidase gene, three restriction enzymes sites, and the coding region for 6 histidine residues. Thus this vector should allow for the inducible expression of foreign genes cloned within it, while also permitting simple purification of the recombinant protein by virtue of the polyhistidine tag. In order to validate the system, the coding region of the *M. leprae* 35 kDa protein was amplified and cloned into the BamHI/XbaI sites of pJAM2 to give plasmid pJAM4. This protein is a major antigen of *M. leprae* and represents a promising candidate as a leprosy-specific diagnostic reagent (Triccas et al., 1996). Plasmid pJAM4 was introduced into *M. smegmatis* mc²155, and recombinant colonies grown in minimal media containing 2% succinate in the presence or absence of 2% acetamide. Sonicates were prepared and proteins analyzed by SDS-PAGE. As shown in FIG. 10A, a prominent band was visible at around 37 kDa in cells grown in acetamide plus succinate (lane 2), but absent from cells grown in succinate alone (lane 1). This band reacted in immunoblotting with mAb CS38, which is raised against the native *M. leprae* 35 kDa protein (FIG. 10B, lane 2).

Figure 11:
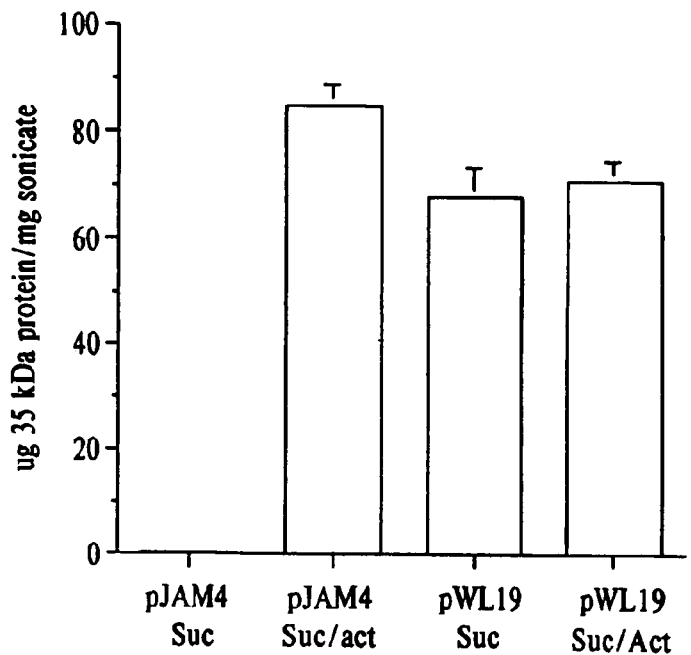

Quantifying Expression of Recombinant Protein in *M. smegmatis* using the pJAM2 Vector In order to quantify the level at which the 35 kDa protein was being produced by virtue of the acetamidase promoter in *M. smegmatis*/pJAM4, antigen-capture ELISA was employed. As shown in FIG. 11, no protein was detected in *M. smegmatis*/pJAM4 grown in succinate alone. When the same strain was grown in the presence of acetamide, the 35 kDa protein represented approximately 8.6% of the total bacterial sonicate. The strength of expression was highlighted through comparison with protein levels in *M. smegmatis* harboring plasmid pWL19 (Winter et al., 1995), where expression of the 35 kDa protein-gene is driven by the β-lactamase promoter of *Mycobacterium fortuitum*, one of the strongest mycobacterial promoters characterized to date (Timm et al., 1994; Timm et al., 1994b). While *M. smegmatis*/pWL19 produced high levels of 35 kDa protein, representing 7.1% of the bacterial sonicate, this was around 17% less recombinant protein than that detected in *M. smegmatis*/pJAM4.

Purification of Histidine-Tagged Protein from Recombinant *M. smegmatis*

We next determined if the high-level expression by virtue of the *M. smegmatis* acetamidase promoter could allow efficient purification of the 35 kDa protein using the 6 histidine residues attached to its C-terminus. This system has been successfully used in a number of eucaryotic and procaryotic expression systems, and is favored due its simple and reliable purification procedure, coupled with minimal effects of the histidine tag on the target protein conformation, function, and immunogenicity (Crowe et al., 1994). Although this system had not been used in mycobacteria before, it seemed an ideal choice to allow the simple and rapid purification of structurally and immunologically intact recombinant mycobacterial proteins. Sonicates of *M. smegmatis*/pJAM4 grown in the presence of acetamide were added to Ni-NTA resin (Qiagen Inc., Calif.), the column washed consecutively with varying amounts of imidazole (5 mM, 20 mM and 40 mM) and protein eluted with 200 mM imidazole. This single-step procedure allowed 35 kDa protein of predominantly a single species to be purified (FIG. 10A, lane 3). The purified product reacted with the anti-*M. leprae* 35 kDa protein mAb CS38 (FIG. 10B, lane 3). Therefore the strategy of Ni-NTA affinity chromatography by virtue of a polyhistidine tag can be utilized for the efficient purification of recombinant proteins from mycobacteria.

Analysis of the Effect of the Histidine Tag on Recombinant Protein Conformation and Immunogenicity Previously it was demonstrated that recombinant forms of the *M. leprae* 35 kDa protein will only react with sera from leprosy patients if the protein is produced in a conformation that resembles that of the native antigen (Triccas et al., 1996). This property allowed us to test the effect, if any, of the histidine tag on the conformation of the recombinant 35 kDa protein. Three preparations of recombinant 35 kDa protein were used: the histidine-tagged version purified in this study, a nonhistidine-tagged version purified from *M.* smegmatis, and an *E. coli* 35 kDa 6-histidine fusion protein. The two latter proteins were purified as described previously (Triccas et al., 1996). The binding of pooled lepromatous leprosy sera to these three forms of the 35 kDa protein were assessed by ELISA. The sera did not react with the *E. coli* form of the 35 kDa protein (FIG. 12). By contrast, the 35 kDa-histidine fusion protein purified from *M. smegmatis/pJAM*4 was strongly recognized by the sera. Furthermore, similar reactivity was exhibited towards the same protein purified from *M. smegmatis* containing no additional histidine residues, suggesting that the addition of the histidine tag had no apparent effect on the conformation and indeed immunogenicity of the recombinant protein.

Induction and Over-Expression of the Gene Encoding the *M. Tuberculosis* DES Antigen Using the pJAM2 Expression System To demonstrate that pJAM2 can be used for the induction and expression of other genes placed within it, we cloned the gene encoding the *M. tuberculosis* DES antigen into the BamHI/XbaI sites of the vector, to give pJAM21. The DES antigen is an immunodominant B-cell antigen with significant sequence similarity to plant acyl-acyl carrier protein desaturases (Jackson et al, 1997). As assessed by immunoblot, no expression of the DES gene was observed in *M. smegmatis* alone grown in the presence or absence of acetamide (FIG. 13, lanes 1 and 2), or by *M. smegmatis* harboring pJAM21 (strain MYC1553) grown in the absence of acetamide (FIG. 13, lanes 3 and 5). By contrast, the DES antigen was readily detected in sonicates of MYC1553 grown in the presence of 2% acetamide (FIG. 13, lanes 4 and 6). These results indicate that high-level induction of the des gene could be achieved by use of the pJAM2 expression system.

The references cited herein are listed on the following pages and are expressly incorporated by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

BIBLIOGRAPHY

1. Altschul, S. F., W. Gish, W. Miller, E. M. Myers, and D. J. Lipman. 1990. Basic local alignment search tool. Journal of Molecular Biology. 215:403–410.
2. Anderson, A. B., and B. Brennan. 1994. Proteins and antigens of *Mycobacterium tuberculosis*, p. 307–332. In B. R. Bloom (ed.), Tuberculosis: Pathogenesis, Protection, and Control. ASM, Washington, D.C.
3. Andersen, P. 1994. Effective vaccination of mice against *Mycobacterium tuberculosis* infection with a soluble mixture of secreted mycobacterial proteins. Infect. Immun. 62:2536–2544.
4. Berthet, F. X., J. Rauzier, E. M. Lim, W. Philipp, B. Giequel, and D. Portnoī. 1995. Characterization of the *M. tuberculosis* erp gene encoding a potential cell surface protein with repetitive structures, Microbiology. 141:2123–2130.
5. de Boer, H. A., Comstock, L. J. and Vasser, M. 1983. The tac promoter: a functional hybrid derived from the trp and lac promoters. Proc. Natl. Acad. Sci. USA 80, 21–25.
6. Braibant, M., L. D. Wit, P., Peirs, M. Kalai, J. Ooms, A. Drowart, K. Huygen, and J. Content. 1994. Structure of the *Mycobacterium tuberculosis* antigen 88, a protein related to the *Escherichia coli* PstA periplasmic phosphate permease subunit. Infection and Immunity. 62:849–854.
7. Cahoon, E. B., Lindqvist Y., Schneider, G., Shanklin, J. 1997. Redesign of soluble fatty acid desaturases from plants for altered substrate specificity and double bond position. Proc. Nat'l. Acad. Sci. USA 94(10), pp. 4872–4877.
8. Crowe, J., Dobeli, H., Gentz, E., Hochilu, E., Stuber, D. and Henco, K. 1994. 6×HIS-Ni-NTA chromatography as a superior technique in recombinant protein expression/purification. Methods Mol. Biol. 31, 371–387.*
9. Fox, B. G., J. Shanklin, J. Ai, T. M. Loerh, and J. Sanders-Loerb. 1994. Resonance Raman evidence for an Fe—O—Fe center in stearoyl-ACP desaturase. Primary sequence identity with other diiron-oxo proteins. Biochemistry. 33:12776–12786.
10. Fulco, A. J., and K. Bloch. 1962. Cofactor requirements for fatty acid desaturation in *Mycobacterium phlei*. Biochim. Biophys. Acta. 63:545-5-46.
11. Fulco, A. J., and K. Bloch. 1964. Cofactor requirements for the formation of Δ9 unsaturated fatty acids in *Mycobacterium phlei*. The Journal of Biological Chemistry. 239–993–997.
12. Garbe, T., Harris, D., Vordermeier, M., Lathigra, R., Ivanyi, J. and Young, D. 1993. Expression of the *Mycobacterium tuberculosis* 19-kilodalton antigen in *Mycobacterium smegmatis*: immunological analysis and evidence of glycosylation. Infect. Immun. 61, 260–267.
13. Gordon, S., Parish, T., Roberts, I. S. and Andrew, P. W. 1994. The application of luciferase as a reporter of environmental regulation of gene expression in mycobacteria. Lett. Appl. Microbiol. 19, 336–340.
14. Haslov, K., A. Andersen, S. Nagai, A. Gottschau, T. Sorensen, and P. Andersen. 1995. Guinea pig cellular immune responses to proteins secreted by *Mycobacterium tuberculosis*. Infection and Immunity. 63:804–810.
15. Hatfull, G. F, 1993. Genetic transformation of mycobacteria. Trends in microbiology. 1:310–314.
16. Hermans, P. W. M., F. Abebe, V. I. O. Kuteyi, A. H. J. Kolk, J. E. R. Thole, and M. Harboe. 1995. Molecular and immunological characterization of the highly conserved antigen 84 from *Mycobacterium tuberculosis* and *Mycobacterium leprae*. Infection and Immunity. 63:954–960.
17. Horburgh, C. R. 1991. *Mycobacterium avium* complex infections in the acquired immunodeficiency syndrome. New England, Journal of Medicine, Vol. 34, pages 1332–1338.
18. Izard, J. W., and D. A. Kendall. 1994. Signal peptides: exquisitely designed transport promoters. Molecular Microbiology. 13:765–773.
19. Jackson, M., Portnoī, D., Catheline, D., Dumail, L., Rauzier, J., Legrand, P. and Gicquel, B. 1997. *Mycobacterium tuberculosis* DES protein: an immunodominant target for the humoral immune response of tuberculosis patients. Infect. Immun. 65, 2883–2889.
20. Jacobs, W. R., G. V. Kalpana, J. D. Cirillo, L. Pascopella, S. B. Snapper, R. A. Udani, W. Jones, R. G. Barletta, and B. R. Bloom. 1991. Genetic systems for mycobacteria. Methods Enzymol. 204:537–555.
21. Kasbiwabara, Y., H. Nakagawa, G. Matsuki, and R. Sato. 1975. Effect of metal ions in the culture medium on the stearoyl-Coenzyme A desaturase activity of *Mycrobacterium phlei*. J. Biochem. 78:803–810.
22. Kashiwabara, Y., and R. Sato. 1973. Electron transfer mechanism involved in stearoyl-coenzyme A desaturation by particulate fraction of *Mycrobacterium phlei*. J. Biochem. 74:405–413.

23. Keegstra, K., and L. J. Olsen. 1989. Chloroplastic precursors and their transport across the envelope membranes. Ann. Rev. Plant Physiol. Plant Mol. Biol. 40:471–501.
24. Laemmli, U. K. 1970. Cleavage of structural proteins during the assembly of the head of bacteriophage T4. Nature (London). 227:680–685.
25. Lee, B. Y., S. A. Hefta, and P. J. Brennan. 1992. Characterization of the major membrane protein of virulent *Mycobacterium tuberculosis*. Infection and Immunity. 60:2066–2074.
26. Legrand, P., and A. Bensadoun. 1991. Stearoyl-CoA desaturase activity in cultured rat hepatocytes. Biochimica et Biophysica Acta. 1086:89–94.
27. Lim, E. M., J. Rauzier, J, Timm, G. Torrea, A. Murray, B. Gicquel, and D. Portnoï. 1995. Identification of *Mycobacterium tuberculosis* DNA sequences encoding exported proteins by using phoA gene fusions. Journal of Bacteriology. 177:59–65.
28. Lindqvist, Y., Huang, W., Schneider, G., Shanklin, J. 1996. Crystal structure of delta9 stearoyl-acyl carrier protein, desaturase from castor seed and its relationship to other di-iron proteins. EMBO. 15(16):4081–92.
29. Mahenthiralingam, E., Draper, P., Davis, E. O. and Colston, M. J. 1993. Cloning and sequencing of the gene which encodes the highly inducible acetamidase of *Mycobacterium smegmatis*. J. Gen. Microbiol. 139, 575–583.
30. Pal, P. G., and M. A. Horwitz: 1992. Immunization with extracellular proteins of *Mycobacterium tuberculosis* induces cell-mediated immune responses and substantial protective immunity in a guinea pig model of pulmonary tuberculosis. Infection and Immunity. 60:4781–4792.
31. Parish, T., Mahenthiralingam, E., Draper, P., Davis, E. O. and Colston, M. J. 1997. Regulation of the inducible acetamidase gene of *Mycobacterium smegmatis*. Microbiology 143, 2267–2276.
32. Parish, T. and Stocker, N. G. 1997b. Development and use of a conditional antisense mutagenesis system in mycobacteria. FEMS Microbiol. Lett. 154, 151–157.
33. Pelicic et al.: 1997. Efficient allelic exchange and transposon mutagenesis in *mycobacterium tuberculosis*. Proc. Natl. Acad. Sci. USA, 94:10955–10960.
34. Pelicic et al.: 1996. Generation of unmarked directed mutations in mycobacteria, using sucrose counter-selectable suicide vectors. Mol. Microbiol., 20:919–925.
35. M. Picardeau and V. Vincent: 1995. Development of a species-specific probe for *Mycobacterium xenopi* Res. Microbiol., 46:237–263.
36. Roche, P. W., Winter, N., Triccas, J. A., Feng, C. and Britton, W. J. 1996. Expression of *Mycobacterium tuberculosis* MPT64 in recombinant *M. smegmatis*: purification, immunogenicity and application to skin tests for tuberculosis. Clin. Exp. Immunol. 103, 226–232.
37. Romain, F., A. Laqueyrerie, P. Militzer, P. Pescher, P. Chavarot, M. Lagranderiet, G. Auregan, M. Gheorghiu, and G. Marchal. 1993. Identification of a *Mycobacterium bovis* BCG 45/47-kilodalton antigen complex, an immunodominant target for antibody response after immunization with living bacteria. Infection and immunity. 61:742–750.
38. Sakamoto, T., H. Wada, I. Nishida, M. Ohmori, and N. Murata. 1994. Δ9 acyl lipid desaturases of cyanobacteria. J. Biol. Chem. 269:25576–25580.
39. Sambrook, J., E. F. Fritsch, and T. Maniatis. 1989. Molecular cloning—A laboratory manual. Cold Spring Harbor Laboratory Press, Cold Spring Harbor, N.Y.
40. Sanger, F., S. Nicklen, and A. R. Coulson. 1977. DNA sequencing with chain terminating inhibitors. Proc. Natl. Acad. Sci. USA. 74:5463–5467.
41. Shanklin, J., and C. Somerville. 1991. Stearoyl-acyl-carrier-protein desaturase from higher plants is structurally unrelated to the animal and fungal homologs. Proceeding of the National Academy of Science of the United States of America. 88:2510–2514.
42. Shanklin, J., E. Whittle, and B. G. Fox. 1994. Eight histidine residues art catalytically essential in a membrane-associated iron enzyme, stearoyl-CoA desaturase, and are conserved in alkane hydroxylase and xylene mono-oxygenase. Biochemistry. 33:12787–12794.
43. Snapper, S. B., B. R. Bloom, and J. W. R. Jacobs. 1990. ¦Molecular genetic approaches to mycobacterial investigation. p. 199–218. In J. McFadden (ed.), Molecular Biology of the Mycobacteria. Surrey University Press, London.
44. Sorensen, A. L., S. Nagai, G. Houen, P. Andersen, and A. B. Andersen. 1995. Purification and characterization of a low-molecular-mass T-cell antigen secreted by *Mycobacterium tuberculosis*. Infection and Immunity. 63:1710–1717.
45. Southern, E. M. 1975. Detection of specific sequences among DNA fragments separated by gel electrophoresis. J. Mol. Biol. 98:503–517.
46. Studier, W., A. H. Rosenberg, J. J. Dunn, and J. W. Dubendorff. 1990. Use of T7 RNA polymerase to direct expression of cloned genes. Methods in Enzymology. 185:60–89.
47. Thole, J. E. R., and R. v. d. Zee. 1990. The 65 kDa antigen: molecular studies on a ubiquitous antigen., p. 37–66. In J. McFadden (ed.). Molecular Biology of the mycobacteria. Surrey University Press. London.
48. Timm, J., Lim, E. M. and Gicquel, B. 1994b. *Escherichia coli*-mycobacteria shuttle vectors for operon and gene fusions to lacZ: the pJEM series. J. Bacteriol. 176, 6749–6753.
49. Timm, J., Perilli, M. G., Duez, C., Trias, J., Orefici, G., Fattorini, L., Amicosante, G., Oratore, A., Joris, B., Frere, J. M., Pugsley, A. P. and Gicquel, B. 1994. Transcription and expression analysis, using lacZ and phoA gene fusions, of *Mycobacterium fortuitum* b-lactamase genes cloned from a natural isolate and a high-level b-lactamase producer. Mol. Microbiol. 12, 491–504.
50. Triccas, J. A., Roche, P. W., Winter, N., Feng, C. G., Butlin, C. R. and Britton, W. J. 1996. A 35 kDa protein is a major target of the human immune response to *Mycobacterium leprae*. Infect. Immune. 64: 5171–5177.
51. Wheeler, P. R., and C. Ratledge. 1994. Metabolism of *Mycobacterium tuberculosis*, p. 353–385. In B. R. Bloom (ed.), Tuberculosis: Pathogenesis, Protection, and Control. ASM, Washington, D.C.
52. Winter, N., Triccas, J. A., Rivoire, B., Pessolani, M. C. V., Eiglmeier, K., Hunter, S. W., Brennan, P. J. and Britton, W. J. 1995. Characterization of the gene encoding the immunodominant 35 kDa protein of *Mycobacterium leprae*. Mol. Microbiol. 16, 865–876.
53. Young, D., T. Garbe, R. Lathigra, and C. Abou-Zeid. 1990. Protein antigens: structure, function and regulation, p. 1–35. In J. McFadden (ed.). Molecular biology of mycobacteria. Surrey university Press, Laudon.
54. Young, R. A., B. R. Bloom, C. M. Grossinsky, J. lvany, D. Thomas, and R. W. Davis. 1985. Dissection of the *Mycobacterium tuberculosis* antigens using recombinant DNA. Proc. Natl. Acad. Sci. USA. 82:2583–2587.

What is claimed is:

1. A plasmid selected from the group consisting of pJAM2 and pJAM21.

2. A recombinant mycobacterium host cell, comprising a plasmid according to claim 1.

3. The recombinant mycobacterium host cell according to claim 2, wherein the plasmid is pJAM2.

4. The recombinant mycobacterium host cell according to claim 2, wherein the plasmid is pJAM21.

* * * * *